(12) United States Patent
Vale et al.

(10) Patent No.: US 11,944,327 B2
(45) Date of Patent: Apr. 2, 2024

(54) EXPANDABLE MOUTH ASPIRATING CLOT RETRIEVAL CATHETER

(71) Applicant: NEURAVI LIMITED, Galway (IE)

(72) Inventors: David Vale, Galway (IE); Ronald Kelly, Galway (IE); Brendan Casey, Galway (IE); Karl Keating, Galway (IE)

(73) Assignee: NEURAVI LIMITED, Galway (IE)

( * ) Notice: Subject to any disclaimer, the term of this patent is extended or adjusted under 35 U.S.C. 154(b) by 234 days.

(21) Appl. No.: 16/809,795

(22) Filed: Mar. 5, 2020

(65) Prior Publication Data
US 2021/0275197 A1 Sep. 9, 2021

(51) Int. Cl.
*A61B 17/22* (2006.01)
*A61M 25/00* (2006.01)
*A61B 17/00* (2006.01)

(52) U.S. Cl.
CPC ......... *A61B 17/22* (2013.01); *A61M 25/0074* (2013.01); *A61B 2017/0084* (2013.01); *A61B 2017/22079* (2013.01)

(58) Field of Classification Search
CPC . A61B 17/22; A61B 17/221; A61B 2017/008; A61B 2017/22079; A61B 2017/2215; A61B 2017/00853; A61B 2017/00862; A61B 2017/22001; A61B 2217/005; A61M 25/0074
See application file for complete search history.

(56) References Cited

U.S. PATENT DOCUMENTS

| | | | |
|---|---|---|---|
| 4,243,040 A | 1/1981 | Beecher | |
| 4,324,262 A | 4/1982 | Hall | |
| 4,351,342 A | 9/1982 | Wiita et al. | |
| 4,575,371 A | 3/1986 | Nordqvist et al. | |

(Continued)

FOREIGN PATENT DOCUMENTS

| AU | 2015271876 B2 | 9/2017 |
|---|---|---|
| CN | 1658920 A | 8/2005 |

(Continued)

OTHER PUBLICATIONS

US 6,348,062 B1, 02/2002, Hopkins (withdrawn)
(Continued)

*Primary Examiner* — Brooke Labranche
(74) *Attorney, Agent, or Firm* — TROUTMAN PEPPER HAMILTON SANDERS LLP

(57) ABSTRACT

A system has an outer catheter and an inner aspirating clot retrieval catheter having an expansile distal tip for flow restriction, improved aspiration efficiency, and a large mouth into which a clot or other obstructions can be retrieved. The clot retrieval catheter can have a support tube proximal of the tip. The expansile tip can be a strut framework, and a flexible, low-modulus cover is disposed around at least a portion of the tip strut framework and the proximal support tube. The distal end of the tip can be encapsulated by a low-friction elastomeric lip for atraumatic contact with the walls of a blood vessel. The tip has a collapsed delivery configuration and expands radially into a deployed configuration. The tip strut framework, support tube, and cover can all have characteristics which enhance the deliverability of the clot retrieval catheter to the target.

19 Claims, 25 Drawing Sheets

(56) References Cited

U.S. PATENT DOCUMENTS

| | | |
|---|---|---|
| 4,592,356 A | 6/1986 | Gutierrez |
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A | 11/1993 | Engelson |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A | 2/1997 | Ton |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,846,251 A | 12/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,142,957 A | 11/2000 | Diamond et al. |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,407 B1 | 11/2001 | Zadno-Azizi et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |

(56) References Cited

U.S. PATENT DOCUMENTS

| | | |
|---|---|---|
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Inder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,382,742 B2 | 2/2013 | Hermann et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |

(56) References Cited

U.S. PATENT DOCUMENTS

| | | |
|---|---|---|
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,172,634 B1 | 1/2019 | Horowitz |
| 10,265,086 B2 | 4/2019 | Vale |
| 10,716,915 B2 | 7/2020 | Ogle et al. |
| 10,610,668 B2 | 8/2020 | Burkholz et al. |
| 10,835,271 B2 | 11/2020 | Ma |
| 11,076,879 B2 | 8/2021 | Yee et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1* | 2/2002 | Hogendijk ....... A61B 17/22031 606/200 |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0100847 A1 | 5/2003 | D'Aquanni et al. |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0144689 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbut |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Q. Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059993 A1 | 3/2005 | Ramzipoor et al. |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119524 A1 | 6/2005 | Sekine et al. |
| 2005/0119668 A1 | 6/2005 | Teague et al. |
| 2005/0125024 A1 | 6/2005 | Sepetka |
| 2005/0131449 A1 | 6/2005 | Salahieh et al. |
| 2005/0149111 A1 | 7/2005 | Kanazawa et al. |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0036271 A1 | 2/2006 | Schomer et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |

(56) References Cited

U.S. PATENT DOCUMENTS

| | | |
|---|---|---|
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0179513 A1 | 8/2007 | Deutsch |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239182 A1 | 10/2007 | Glines et al. |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0269774 A1 | 10/2008 | Garcia et al. |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0016957 A1 | 1/2010 | Jager et al. |
| 2010/0030186 A1 | 2/2010 | Stivland |
| 2010/0030256 A1 | 2/2010 | Dubrul et al. |
| 2010/0036312 A1 | 2/2010 | Krolik et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0137846 A1 | 6/2010 | Desai et al. |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305566 A1 | 12/2010 | Rosenblatt et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0025934 A1 | 1/2013 | Aimi et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |

(56) References Cited

U.S. PATENT DOCUMENTS

| | | |
|---|---|---|
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257018 A1 | 9/2014 | Farnan |
| 2014/0257362 A1 | 9/2014 | Eldenschink |
| 2014/0276922 A1 | 9/2014 | McLain et al. |
| 2014/0277003 A1 | 9/2014 | Hendrick |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371777 A1 | 12/2014 | Rudakov et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173782 A1 | 6/2015 | Garrison et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257774 A1* | 9/2015 | Galdonik ............ A61B 17/22 606/127 |
| 2015/0257775 A1 | 9/2015 | Gilvarry et al. |
| 2015/0258270 A1 | 9/2015 | Kunis |
| 2015/0290437 A1 | 10/2015 | Rudakov et al. |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086864 A1 | 3/2017 | Greenhalgh et al. |
| 2017/0086996 A1 | 3/2017 | Peterson et al. |
| 2017/0095138 A1 | 4/2017 | Nakade et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100142 A1 | 4/2017 | Look et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0239447 A1 | 8/2017 | Yang et al. |
| 2017/0252043 A1 | 9/2017 | Fuller et al. |
| 2017/0252064 A1 | 9/2017 | Staunton |
| 2017/0259042 A1 | 9/2017 | Nguyen et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |

(56) References Cited

U.S. PATENT DOCUMENTS

| | | |
|---|---|---|
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193050 A1 | 7/2018 | Hawkins et al. |
| 2018/0193591 A1 | 7/2018 | Jaroch et al. |
| 2018/0235743 A1 | 8/2018 | Farago et al. |
| 2018/0256177 A1 | 9/2018 | Cooper et al. |
| 2018/0303610 A1 | 10/2018 | Anderson |
| 2019/0021755 A1 | 1/2019 | Johnson et al. |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1* | 7/2019 | Barry ................. A61B 17/22 |
| 2019/0239907 A1 | 8/2019 | Brady et al. |
| 2019/0247627 A1 | 8/2019 | Korkuch et al. |
| 2019/0255290 A1 | 8/2019 | Snyder et al. |
| 2019/0269491 A1 | 9/2019 | Jalgaonkar et al. |
| 2019/0274810 A1 | 9/2019 | Phouasalit et al. |
| 2019/0298396 A1 | 10/2019 | Gamba et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2020/0155180 A1 | 5/2020 | Follmer |
| 2020/0214859 A1 | 7/2020 | Sherburne |
| 2020/0281611 A1 | 9/2020 | Kelly et al. |
| 2020/0353208 A1 | 11/2020 | Merhi et al. |
| 2020/0383698 A1 | 12/2020 | Miao et al. |
| 2021/0085935 A1 | 3/2021 | Fahey et al. |
| 2021/0153883 A1 | 5/2021 | Casey et al. |
| 2021/0153884 A1 | 5/2021 | Casey et al. |
| 2021/0154433 A1 | 5/2021 | Casey et al. |
| 2021/0219821 A1 | 7/2021 | Appling et al. |
| 2021/0228223 A1 | 7/2021 | Casey et al. |
| 2022/0117614 A1 | 4/2022 | Salmon et al. |
| 2022/0125450 A1 | 4/2022 | Sirhan et al. |
| 2022/0313426 A1 | 10/2022 | Gifford, III et al. |
| 2023/0054898 A1 | 3/2023 | Gurovich et al. |

FOREIGN PATENT DOCUMENTS

| | | |
|---|---|---|
| CN | 1972728 A | 5/2007 |
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| EP | 4049704 A2 | 8/2022 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |

(56) References Cited

FOREIGN PATENT DOCUMENTS

| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/162678 A1 | 8/2021 |
| WO | WO 2021/167653 A1 | 8/2021 |
| WO | WO 2022/020366 A2 | 1/2022 |

OTHER PUBLICATIONS

Struffert, T., et al. "Intravenous flat detector CT angiography for non-invasive visualisation of intracranial flow diverter: technical feasibility" Eur Radiol 21:1797-1801 (2011).

* cited by examiner

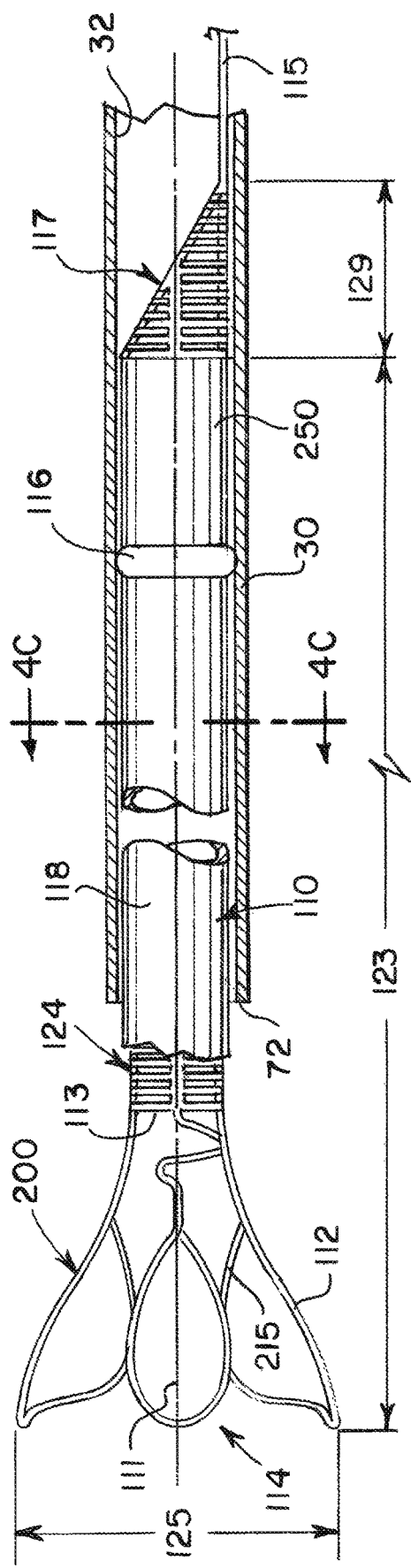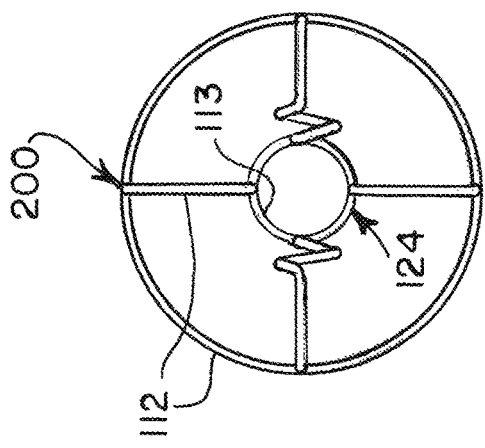

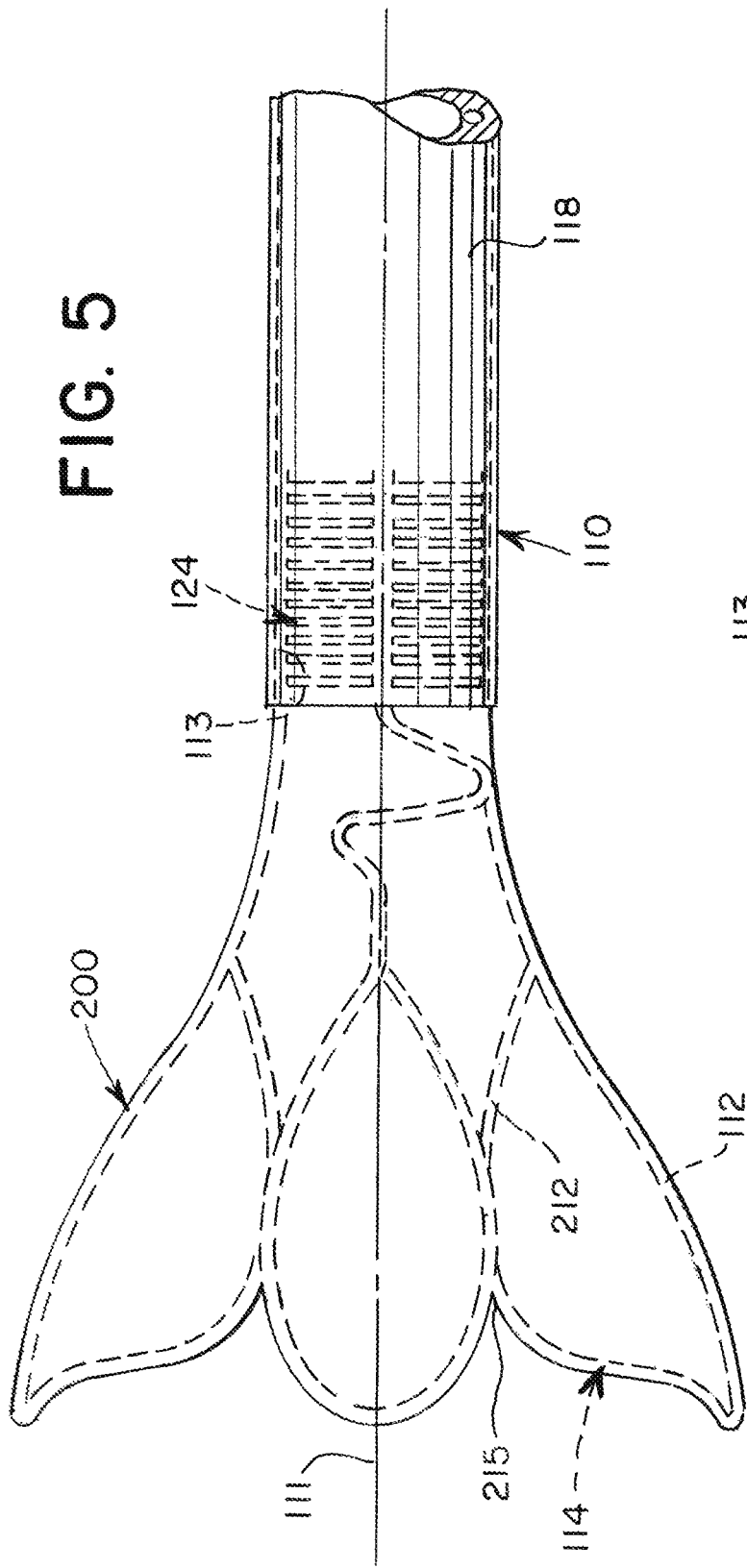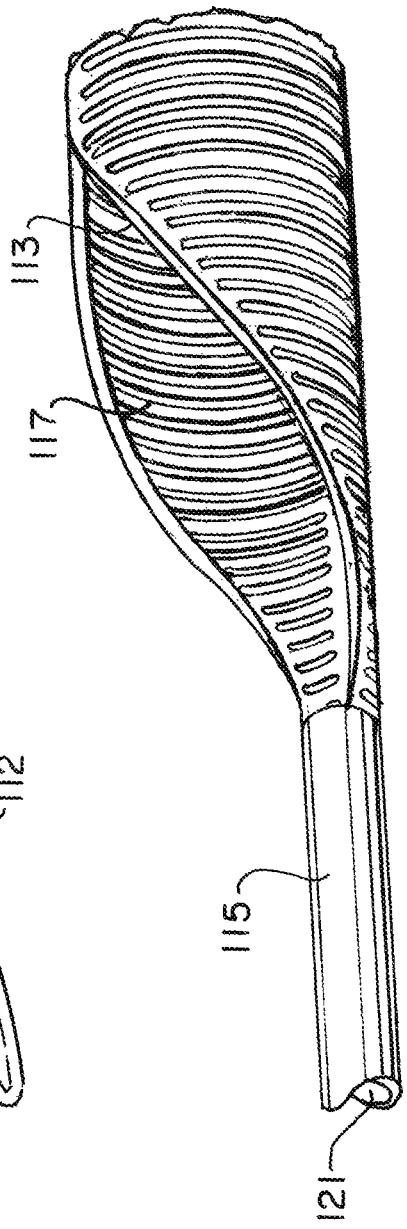

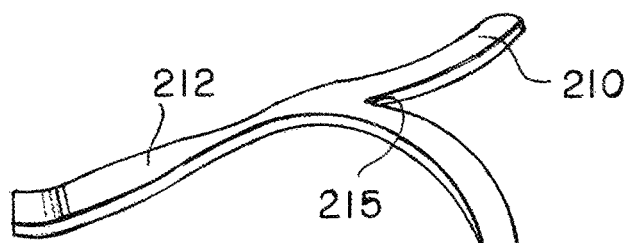
FIG. 12C
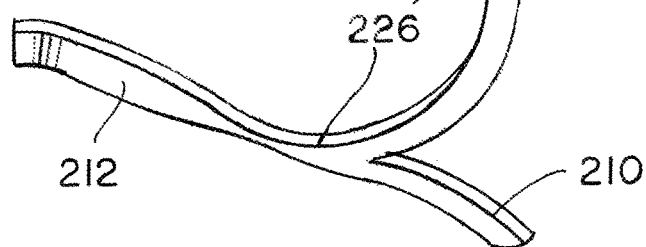
FIG. 12D
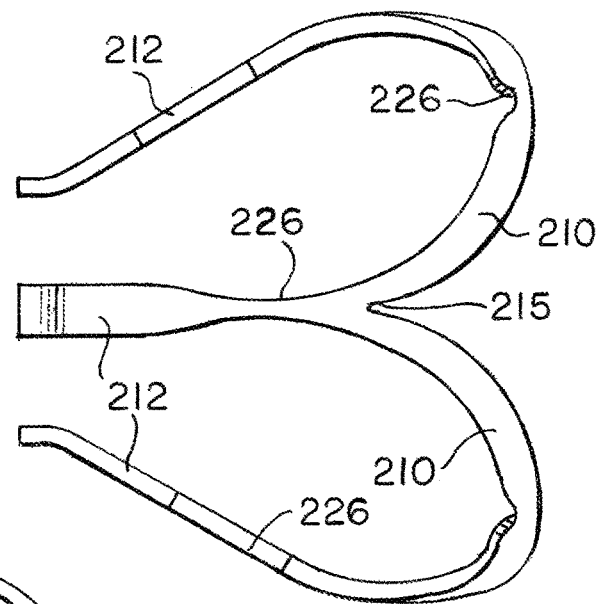
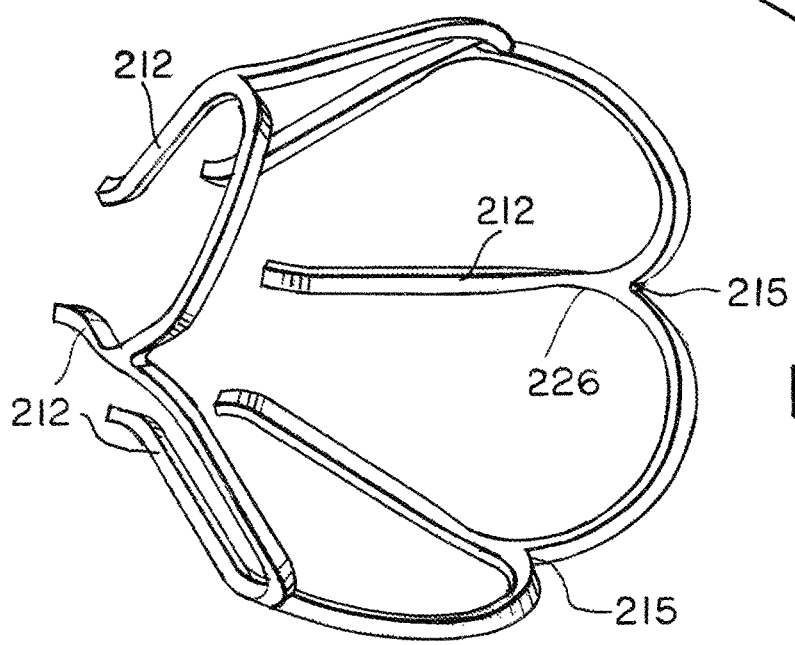
FIG. 13A

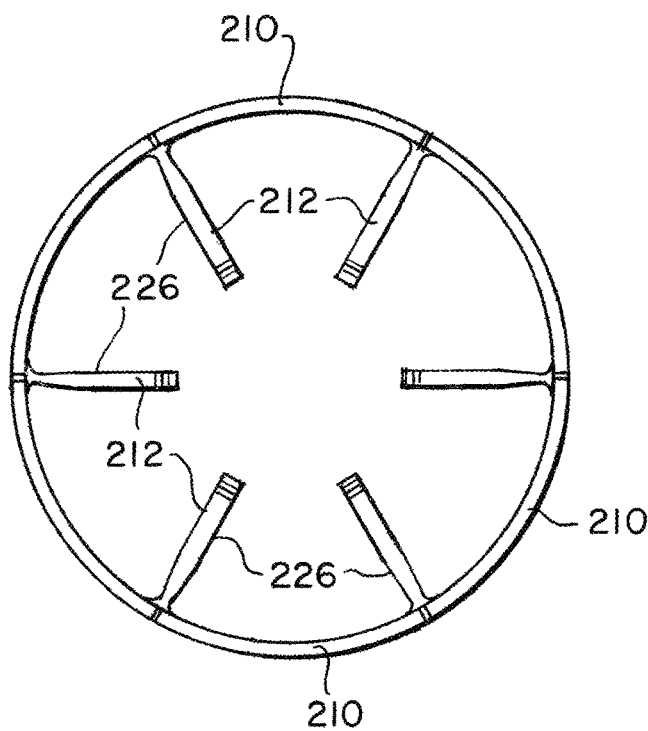
FIG. 13B
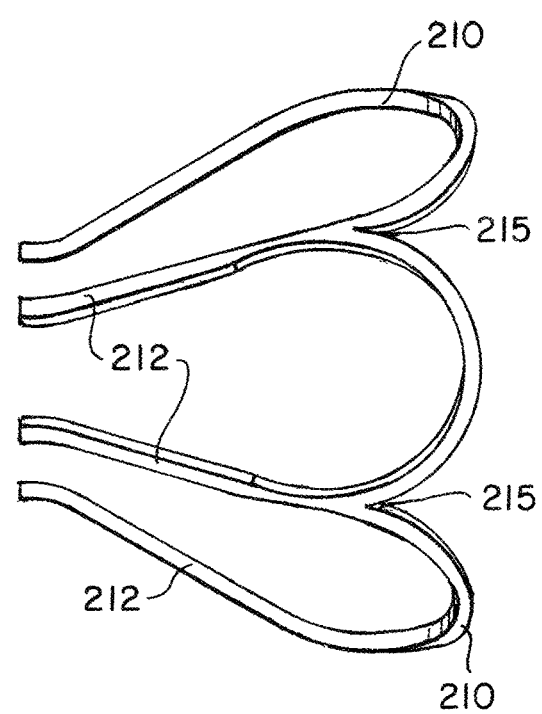
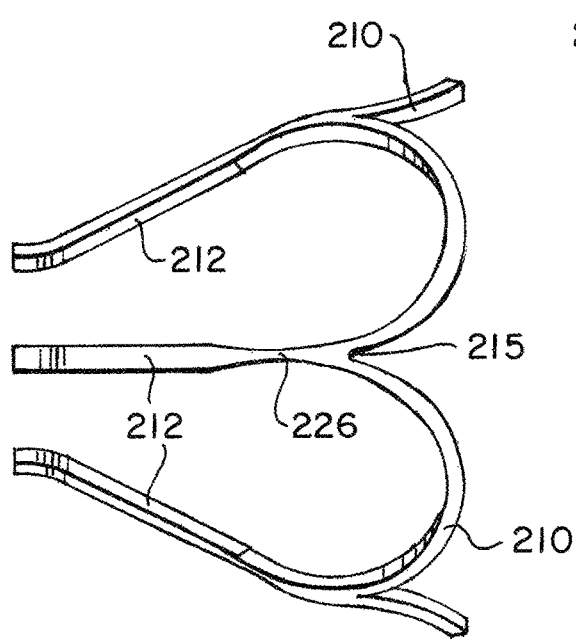
FIG. 13C
FIG. 13D

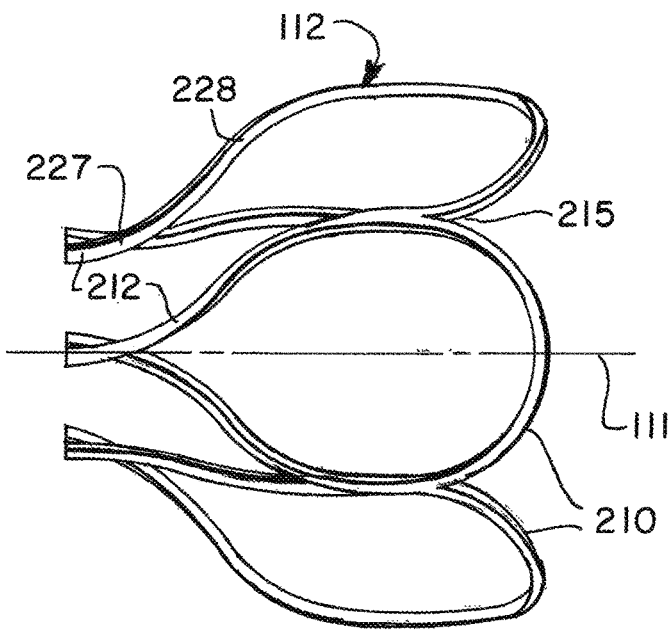
FIG. 16D
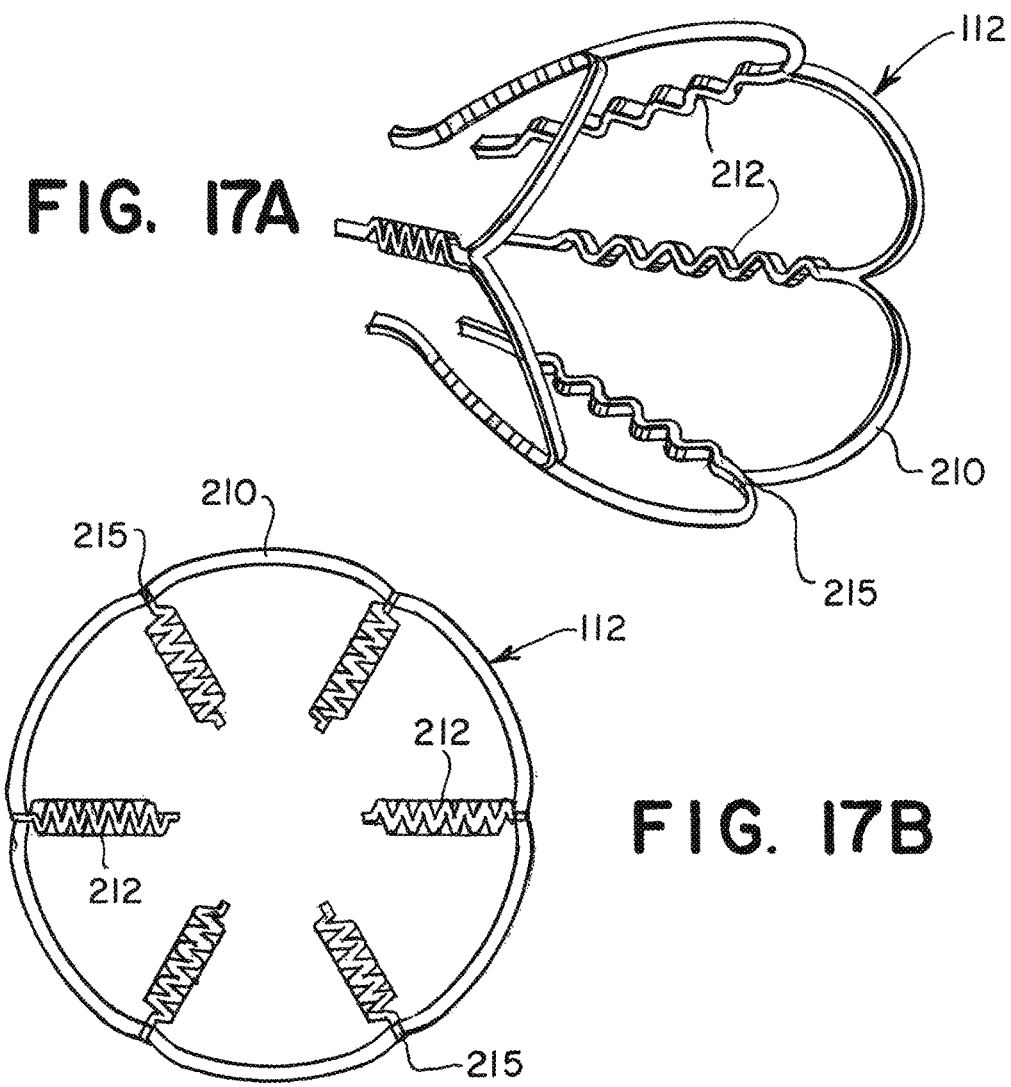
FIG. 17A
FIG. 17B

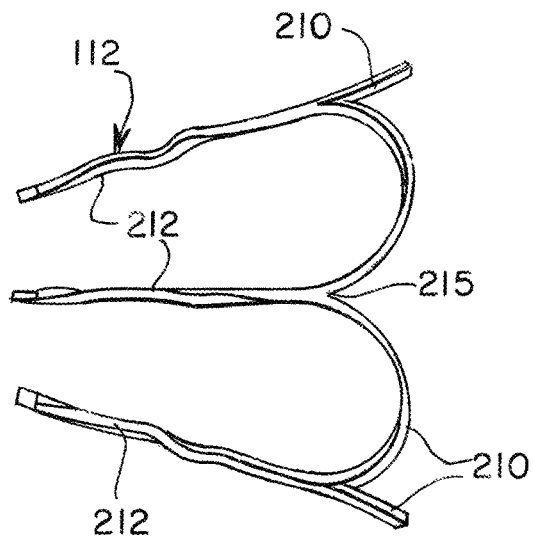
FIG. 20C
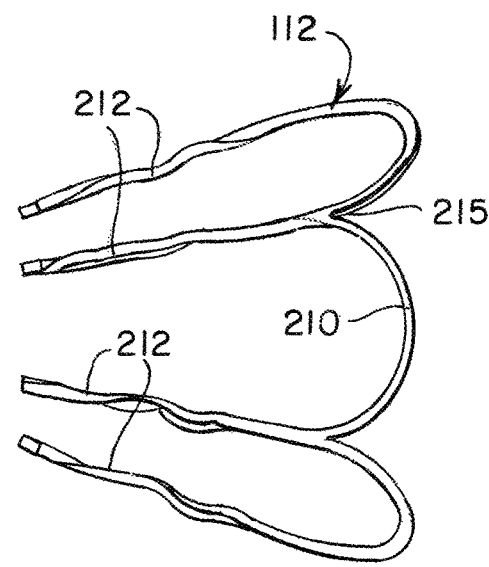
FIG. 20D
FIG. 21A
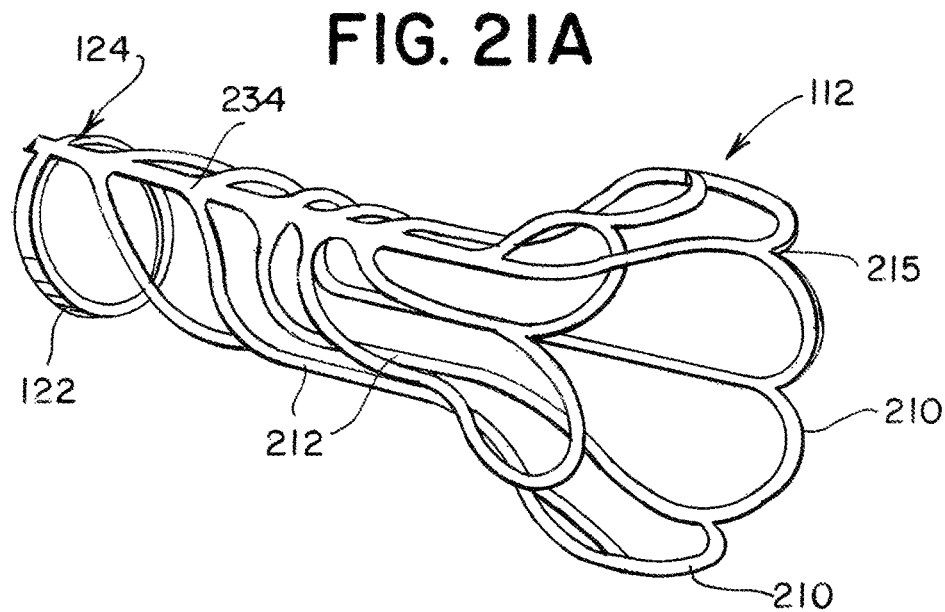

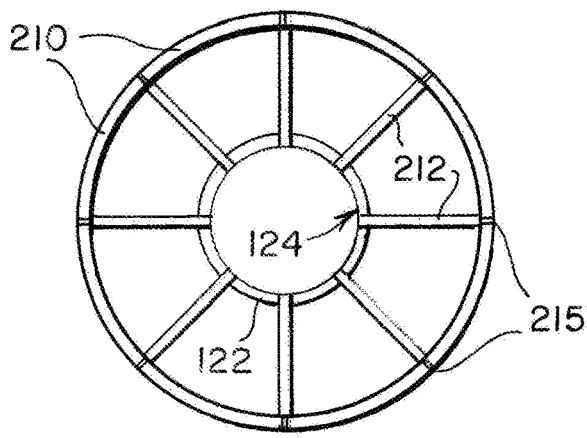
FIG. 21B
FIG. 21C
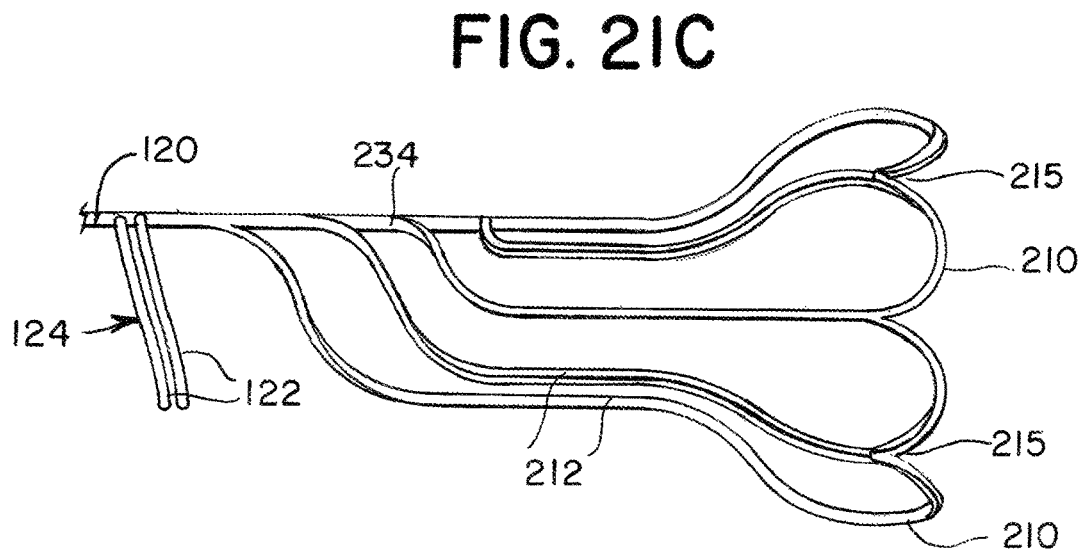
FIG. 21D
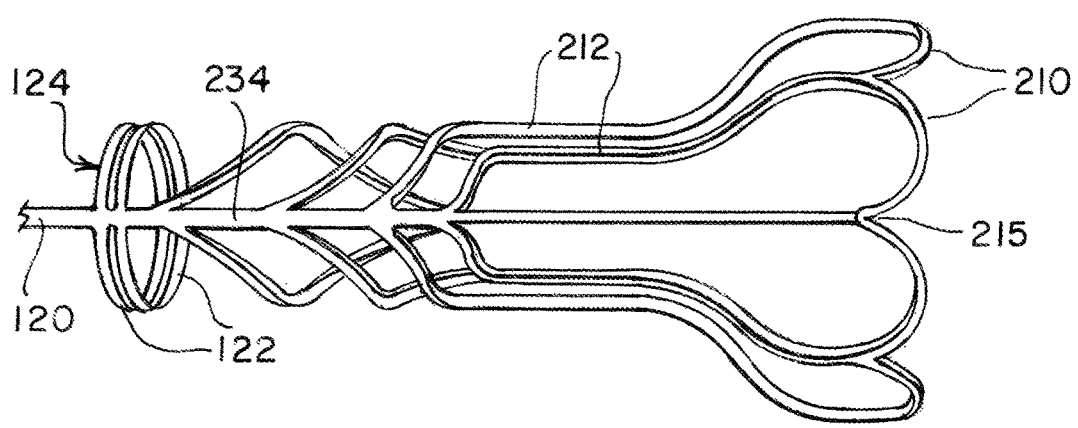

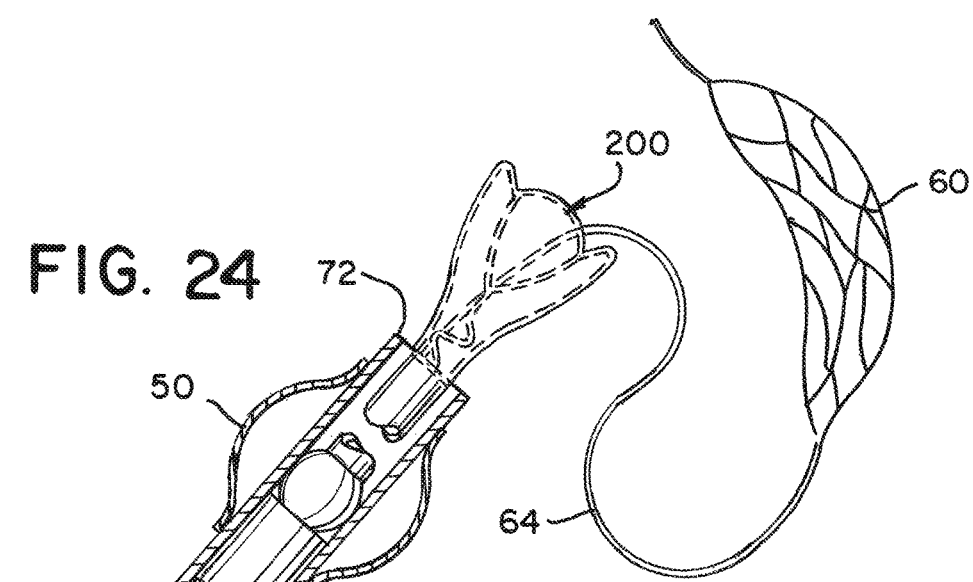
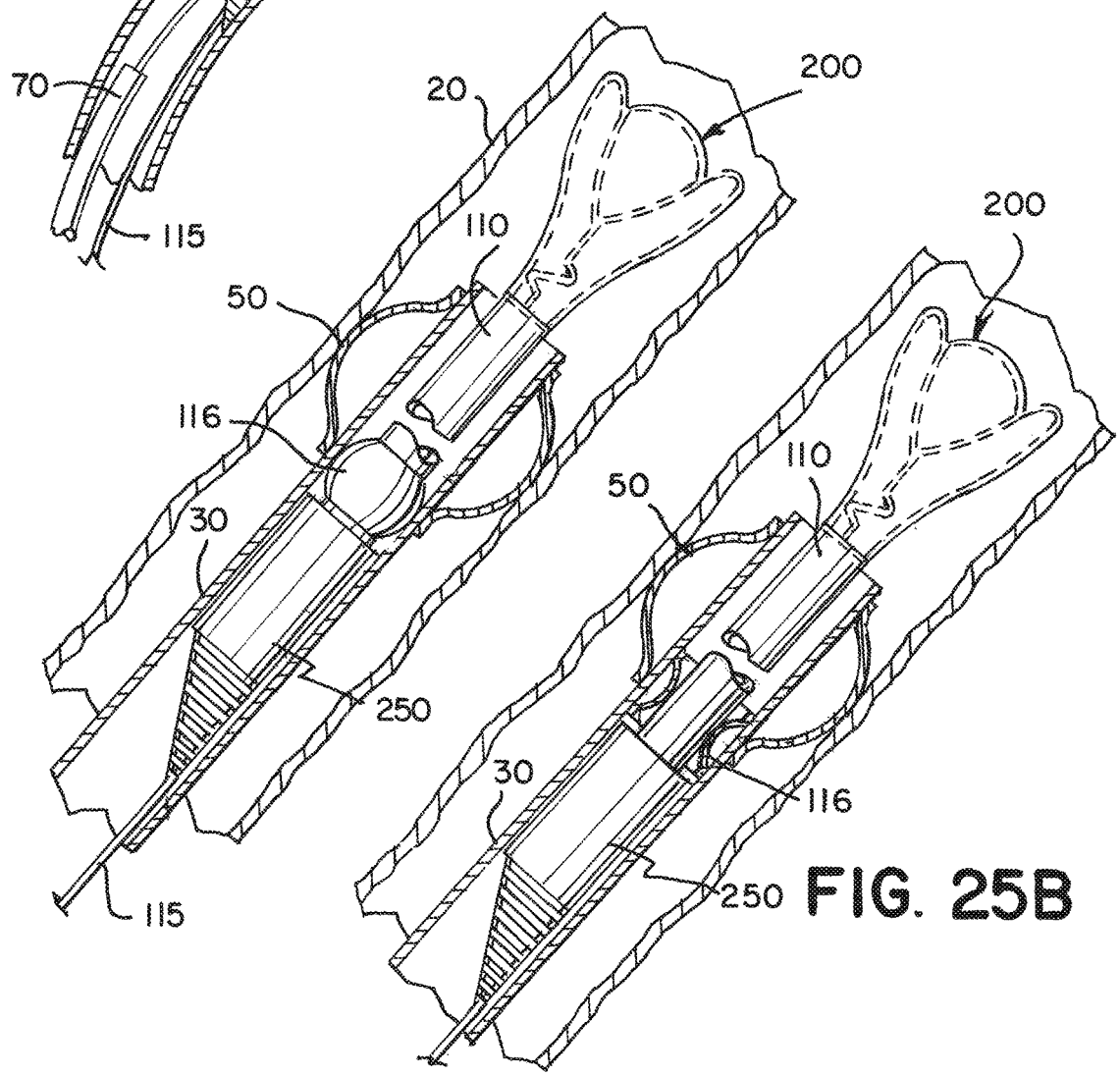

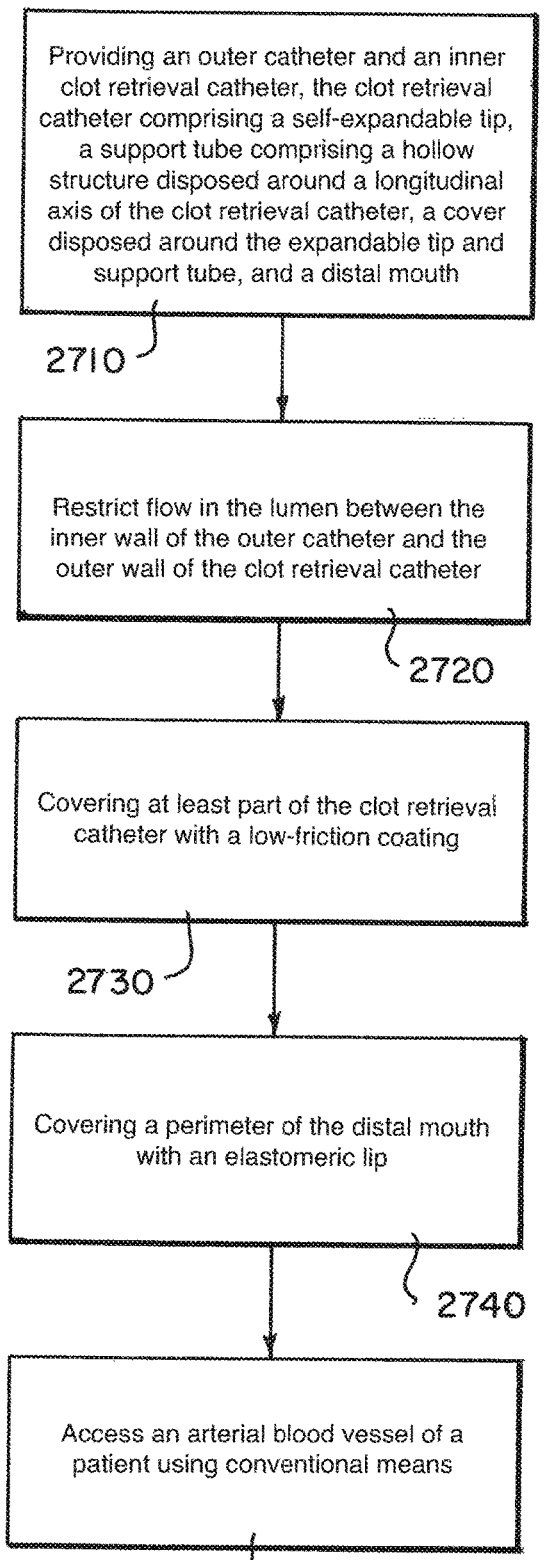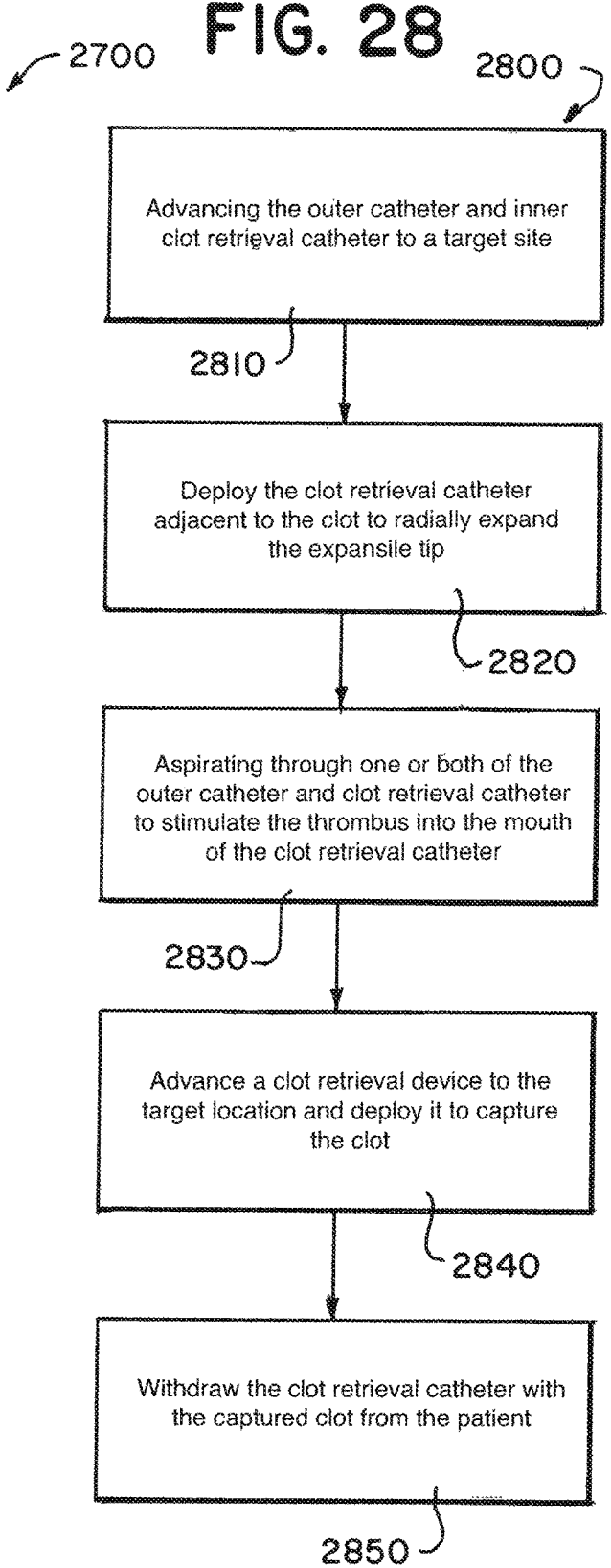

EXPANDABLE MOUTH ASPIRATING CLOT RETRIEVAL CATHETER

FIELD OF THE INVENTION

The present invention generally relates devices and methods for removing acute blockages from blood vessels during intravascular medical treatments. More specifically, the present invention relates to an aspirating retrieval catheter.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing remote areas such as the neurovascular bed is challenging with conventional technology, as the target vessels are small in diameter, distant relative to the site of insertion, and are highly tortuous.

The clot itself can complicate procedures by taking on a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Fibrin rich clots also present a challenge in having a sticky nature that can cause a clot to roll along the outer surface of a mechanical thrombectomy device rather than being gripped effectively. Combinations of soft and firm clot regions can also separate during aspiration, with fragmentation leading to distal embolization which can occur in vessels that cannot be reached with currently available devices. Additionally, breaking the bonds adhering the clot to the vessel wall without damaging fragile vessels is a significant challenge.

Conventional clot retrieval catheters, especially those for operating in the neurovascular, can suffer from a number of drawbacks. First, the diameters of the catheters themselves must be small enough to avoid causing significant discomfort to the patient. The catheter must also be sufficiently flexible to navigate the vasculature and endure high strains, while also having the axial stiffness to offer smooth advancement along the route. Once at the target site, typical objects to be retrieved from the body can be substantially larger in size than the catheter tip, making it more difficult to retrieve objects into the tip. For example, fibrin-rich clots can often be difficult to extract as they can become lodged in the tip of traditional fixed-mouth catheters. This lodging can cause softer portions of the clot to shear away from the firmer regions, leading to distal embolization.

Small diameters and fixed tip sizes can also be less efficient at directing the aspiration necessary to remove blood and thrombus material during the procedure. The aspiration suction must be strong enough such that any fragmentation occurring through the use of a mechanical thrombectomy device or other methods can, at the very least, be held stationary so that fragments cannot migrate and occlude distal vessels. When aspirating with a traditional fixed-mouth catheter, however, a significant portion of the aspiration flow ends up coming from vessel fluid proximal to the tip of the catheter where there is no clot. This significantly reduces aspiration efficiency, lowering the success rate of clot removal.

The disclosed design is aimed at providing an improved aspirating retrieval catheter which addresses the above-stated deficiencies.

SUMMARY

It is an object of the present design to provide systems, devices, and methods to meet the above-stated needs. The design features an aspiration clot retrieval catheter with an expandable clot-facing mouth for flow restriction, aspiration efficiency, and easy retrieval of the clot while also having a collapsed state that is low-profile and sufficiently flexible for delivery in a standard sheath or outer catheter. The catheter can also have a tailored, variable-stiffness body section incorporating deliverability enhancements over existing designs and capable of navigating tortuous areas of the vasculature to reach an occlusive clot.

According to the present invention, there is provided a system which can have an outer catheter facilitating the introduction of microcatheters, guidewires, or any of a number of commercially available products to a target site within the vasculature. The outer catheter can be, for example, a guide catheter or an intermediate catheter. Within the outer catheter can be an aspiration clot retrieval catheter having an expansile distal tip. In one example, the clot retrieval catheter is a rapid exchange (RX) type catheter with an expanding distal tip. RX devices can offer advantages over many over-the-wire products, which can be time consuming to exchange and may have components which extend beyond the sterile field, adding the risk of contamination.

The clot retrieval catheter may have a proximal end, a distal end located at the tip mouth, a proximal port, and an internal lumen extending proximal of the distal end and terminating at the port. The catheter lumen can be defined by a tubular support structure, and can be configured for the passage of guidewires, microcatheters, mechanical thrombectomy devices like stentrievers, and other such devices therethrough. The lumen can also direct aspiration from the proximal end of the outer catheter to the expansile distal tip of the clot retrieval catheter. The clot retrieval catheter can also have a shaft extending proximal to the port.

The clot retrieval catheter can have a self-expanding tip disposed at the distal end of the catheter. The tip can have a collapsed delivery configuration and a radially expanded deployed configuration in which the tip assumes a substantially conical or funnel shape. In the collapsed state, the tip can share a common radial dimension with the outer catheter when folded and constrained during delivery, the radial dimension being less than a maximum radial dimension of the tip when in the expanded deployed state. The tip can have an open distal mouth and at least a portion of the tip can have a maximum radial dimension in the expanded deployed configuration greater than an inner diameter of an outer catheter.

The expansile tip can be connected at its proximal end to a support tube configured around the longitudinal axis of the clot retrieval catheter which defines the inner lumen of the catheter. The support tube can have a series of loop ribs extending laterally to and at various lengths from one or more axially-extending longitudinal spines. The ribs and spines can be monolithically formed though laser machining of a single hypotube or can be of metallic braid or coiled wire construction. The spine can be fixedly connected to, or formed integrally with, a support arm or connecting strut of the expansile tip.

In one example, the support tube shares a common radial dimension with a length of the expansile tip when the tip is in the collapsed delivery configuration. When deployed, the tip can radially expand outward of the support tube. A section of the support tube approximate the proximal end can flare or be sized to a larger diameter to block flow in the lumen between the outer catheter and the clot retrieval catheter.

The expansile tip can have a supporting structure with a plurality of struts formed into a porous framework which can include closed cells, loops, or undulations. A plurality of distal crowns can form the perimeter of the tip mouth. Support arm struts can link adjacent crowns where they meet at proximal crown troughs, and the support arms can extend proximally from the crown troughs to connect the expansile tip with the support tube.

The support arms may be axisymmetric with the longitudinal axis of the catheter, or they can be twisted or situated in a helical fashion about the axis. Individual support arms can attach independently or can extend from or align with one of the one or more axial spines of the support tube. The struts of the crowns and support arms may contain features such as narrowed segments, curves, and/or undulations to enhance the flexibility of the structure. When the tip is in the collapsed delivery configuration the proximal crown troughs can serve as hinges about which the strut framework folds. When folded in the delivery configuration, at least a portion of the expansile tip shares a common radial dimension with the support tube.

The strut framework can be a cut pattern of sheet or tube stainless steel, or a superelastic shape memory alloy such as Nitinol. The shape of the framework can be such that the profile of the tip in the deployed configuration hinges radially outward to have a portion be nearly tangent with the vessel wall. When expanded, at least a portion of the tip will assume a maximum radial size of the expansile tip. The funnel shape formed by the tip can improve aspiration efficiency, reduce friction, and lessen the risk of vessel trauma from snagging on vessel openings. A funnel shape also means in the deployed state the expansile tip is tapered such that a proximal end of the tip has a first radial dimension and a more distal portion of the tip has a second radial dimension larger than the first radial dimension. The second radial dimension can be larger than the diameter of the target blood vessel.

In another example, crowns of the tip framework can form a more atraumatic profile by curving radially inward at the distal mouth. In this situation the distal crown peaks can have a radial dimension between the first radial dimension and the maximum radial size of the expansile tip.

One or more support arms or ligament struts can connect the tip framework with the support tube, either directly or indirectly through eyelets or another loose mechanical joint. The support arms can connect via a single axial connecting strut, or they can extend individually and independently from a base strut or the distalmost rib of the support tube. The support arms can have patterns which increase flexibility, such as undulations or expandable cells. In one example, the tip and support tube can be monolithically formed together. When rigid, the support arms can fix the longitudinal location of the expansile tip relative to the distal end of the support tube. In an alternate example, the support arms can take a waveform shape or have narrowed sections to improve the overall flexibility of the framework.

A flexible cover can be disposed to form a sleeve around at least a part of the support tube and at least a part of the strut framework of the expansile tip. The cover can be formed from a ductile elastomer, which has the advantages of being soft and flexible with resistance to tearing and perforation due to a high failure strain. The cover can encapsulate the tip framework and support tube so that it makes up both the inner and outer surfaces of the catheter. As an alternative, the cover can be one or more polymer jackets which can be fused together and adhered, reflowed, or stitched to the strut framework. The cover can further be coated with or be made from an elastomer or similar material to provide a low-friction surface to facilitate navigation within blood vessels as well as other catheters. If coated, the support tube can be coated both internally and externally with a lubricious film. The coating can be delivered via spray, plasma, or any other commonly used technique. Alternately, the cover or jackets can be impregnated with particles having low-friction properties. These methods can give the deliverability advantages of reducing both the static and dynamic coefficients of friction, lessening frictional interference with the outer catheter and vessel wall. If desired, the properties of the cover can be tailored such that it was semi- or fully permeable.

In another example, the support tube can also have a tubular liner disposed within and lining the lumen of the support tube. Similar to the cover, the liner can be of PTFE and have low-friction properties or impregnated with particles to facilitate smooth delivery of other devices through the clot retrieval catheter and aid the clot in being pulled proximally through the catheter with aspiration and/or mechanical thrombectomy. In the absence of such a liner, the inner surfaces of the support tube structure can still be coated for the same deliverability advantages.

In one aspect of the present design, the maximum diameter of the expansile tip when expanded is larger than the diameter of the associated outer catheter of the system. The radial dimensions approximate the distal end of the expansile tip can be sized to atraumatically contact the circumference of the inner wall of the target vessel. A length of the distal end of the expansile tip can be dip coated to a length of the tip defining a dip zone, thereby forming an atraumatic overhanging elastomeric lip around the crowns and support arms. Dip coating often involves dipping a part in a liquid coating material, such as a hydrogel or a flexible fluoropolymer, and then heating the part in a furnace or heated chamber, where a fusion process permanently bonds the surfaces. Original shore durometer, flexibility, and other tribological properties of a part typically remain unaffected by the dip coating procedure. The dip coating can be tailored to increase the wall thickness of the cover at the tip, where the elastomeric lip forms a soft, protective rim extending around the circumference of the crowns at the distal end of the tip. This process effectively encapsulates at least a part of the strut framework of the tip.

The ribs of the support tube can be a number of shapes and thicknesses and may or may not extend around a complete circumference of the longitudinal axis of the clot retrieval catheter. The number of the ribs along the length of the axial spine or spines can be high enough such that the density of the rib spacing is sufficient to support the ductile and compliant cover. The density of the ribs can also vary at different axial lengths of the support tube.

In some scenarios, such as when retrieving stiff clots with high fibrin content, an aspiration catheter may not be successful in removing all of the clot. In this case, the aspiration clot retrieval catheter can be used in conjunction with a separate mechanical thrombectomy device. The thrombectomy device can be any of a number of commercially-available clot retrieval products. The thrombectomy device may be housed in a microcatheter which is movable relative to the aspiration clot retrieval catheter, and the microcatheter can be used to deploy a clot gripping device from the lumen of the microcatheter. The microcatheter can be disposed within the lumen of the aspiration clot retrieval catheter. The proximal port of the aspiration catheter can facilitate the forwarding of the microcatheter to the target site. The aspiration clot retrieval catheter, microcatheter, and gripping device can be simultaneously delivered to the target site through the outer catheter. Once the target site is reached, the tip of the aspiration clot retrieval catheter can be expanded to the deployed state. The clot gripping device can then be deployed from the microcatheter to engage and capture an occlusive clot while aspirating through the expanded tip of the aspiration clot retrieval catheter.

The system can have one or more aspiration sources for the catheters. An aspiration source can be utilized to prevent blood reflux and to help dislodge and remove thrombus material from the vasculature. Aspiration sources are often connected to a side port of a luer or rotating hemostasis valve assembly to provide and regulate a vacuum to one or more of the catheters while leaving the central lumen free for advancement/retraction of ancillary devices. For example, aspiration can be applied through a side-port of a hemostasis valve connected to an aspiration catheter with simultaneous use of a stent retriever and microcatheter within the lumen of the aspiration catheter to increase the likelihood of a first pass TICI 3 rating. The source can also be attached directly to the proximal end of an outer catheter such that dual aspiration is applied; one aspiration source can aspirate from the distal end of the outer catheter to a proximal end of the outer catheter and a second aspiration source aspirating from the distal end of the expansile tip to a proximal end of the aspirating clot retrieval catheter. The aspiration source may include one or more syringes, or a vacuum pump connected to interface with the distal tip of the catheter(s) through the catheter lumen(s) and aspirate as the clot is being retrieved.

In another example, the aspiration clot retrieval catheter can be an RX catheter that transitions from a distal expansile tip to intermediate tubular section and finally to a proximal wire section. The catheter can be capable of effecting a seal against either or both of the vessel wall and the inner lumen of the outer catheter. The seal with an outer catheter can be a catheter segment with an enlarged or flared diameter to impede flow or can be formed from a molded ring similar to an O-ring. In another instance, a seal can be accomplished by inflating an inflatable balloon-type mechanism. In still another case, the expansile tip can seal against the vessel wall proximal of the clot when deployed to the expanded configuration. The transition from intermediate tube to proximal wire allows for increased aspiration flow rates by maximizing the cross-sectional area available along the length of the catheter, taking advantage of the large proximal lumen provided by the outer catheter. The seal between the RX catheter and outer catheter directs full aspiration power from the proximal end of the outer catheter to the distal end of the expansile tip and eliminates losses of aspiration between that would otherwise occur through a lumen formed between the inner diameter of the outer catheter and the outer diameter of the catheter. The seal at the vessel wall, provided by the expansile tip, allows for more effective aspiration, directing full aspiration power distal of the expansile tip while providing a profiled entry for a clot to be progressively elongated and drawn into the lumen of the catheter and prevent clot shearing and fragmentation. If a separate thrombectomy device is used, the expansile tip also provides a larger opening into which a retrieval device and a captured clot can be withdrawn, lessening the risk of the tip shearing or dislodging the clot or fragments of the clot from the retrieval device. Fragmentation can occur with catheters having a distal mouth with a cross section smaller than that of the clot itself.

If a complete seal is not desired, a flow restrictor can be used between the outer catheter and the clot retrieval catheter. The flow restrictor can have bristles, a dense framework, or some other form which can inhibit flow. The flow restrictor can be located on the inner surface of the outer catheter. Alternatively, the flow restrictor can be located on the outer surface of the clot retrieval catheter distal of the wire to tube transition.

In one case a system can have an outer catheter and an inner aspirating clot retrieval catheter. The clot retrieval catheter can have a support tube which defines a lumen of the clot retrieval catheter and a radially expandable tip linked to the distal end of the support tube. The expandable tip can be monolithically formed with the support tube and the proximal end of the tip can be longitudinally fixed with the distal end of the support tube. The tip can also have an internal lumen in communication with the lumen of the support tube and configured to aspirate a clot.

The expandable tip can have a collapsed state and an expanded state. When collapsed, the tip can have a radial dimension or diameter less than a maximum radial dimension or diameter of the expandable tip, and at least a portion of the tip can share a radial dimension with the support tube. When expanded, the expansile tip grows radially outward from the support tube, with at least a portion of the tip assuming a diameter greater than the diameter of the outer catheter. The tip can further have an open distal end and a lumen for receiving a clot that is in communication with the lumen of the support tube. In the expanded state, the distal end can contact, and form a seal with, the inner wall of the vessel.

In one example, the tip can have a framework with a network of strut members. When the outer catheter is pulled back to actuate the tip to an expanded state, the strut framework takes on a tapered, funnel-shaped form and has a first radial size at the proximal end of the tip framework and a second radial size larger than the first approximate the distal end of the tip framework. Similar to other examples, the network of members can be monolithically formed with the support tube, from a laser cut sheet or drawn wire. Some members can link the expansile tip with the support tube. Additionally, the width of struts in the strut framework can be varied to increase the flexibility of the tip in tortuous areas of the vasculature.

The system can further have a flexible elastomeric cover disposed radially around the support tube and expansile tip of the aspirating clot retrieval catheter. The cover can be homogenous or can have multiple layers. The cover can be coated, both internally and externally, with a low-friction coating, and similarly the network members at the distal end of the expansile tip can be dip coated with the same or a different coating to improve the deliverability qualities of the catheter and create a soft distal ridge to reduce the risk of vessel trauma.

The aspiration clot retrieval catheter can have RX features and have a port with a control member or shaft extending proximally from the port. The port can be configured to transmit aspiration from the proximal lumen of the outer catheter to the distal tip of the aspiration clot retrieval catheter. The shaft of an RX catheter can offer great advantages in terms of speed, deliverability, ease of use, and optimal aspiration flow rates.

Also provided is a method for removing an occlusive thrombus from a blood vessel. The method can have some or all of the following steps and variations thereof, and the steps are recited in no particular order. The method can involve accessing an arterial blood vessel of a patient using conventional means and advancing an outer catheter into the vasculature. An inner clot retrieval catheter can be advanced through the outer catheter, the clot retrieval catheter comprising a self-expandable tip, a support tube comprising a hollow structure disposed around a longitudinal axis of the clot retrieval catheter, a polymeric cover disposed around at least a part of the expandable tip and support tube, and a distal mouth. The self-expandable tip can be sized to contact and seal with the walls of a target vessel when deployed. A further step can involve covering the perimeter of the mouth with a soft lip or rib so as to minimize the risk of vessel trauma.

The outer catheter can be configured to direct the aspiration applied at the proximal end of the outer catheter through the distal lumen of the clot retrieval catheter to aspirate the clot into the mouth of the clot retrieval catheter. In one example, the method can include the step of restricting flow between the outside surface of the clot retrieval catheter and the inside surface of the outer catheter. Flow can also be restricted between the inner wall of the vessel and the outer wall of either the outer catheter or clot retrieval catheter. If desired, a balloon guide catheter can also be used for this purpose.

The cover can be a flexible elastomer or one or more polymer jackets. In a further step, a low-friction liner or coating can be applied to at least a part of the inner and/or outer surfaces of the support tube and expandable tip. The liner can be adhered to the struts and ribs using heat or other suitable means. Giving the catheter surfaces low-friction properties can help the clot retrieval catheter transit through the outer catheter while also facilitating the passage of ancillary devices during a procedure.

The method can continue with the step of advancing the inner clot retrieval catheter through the outer catheter until the expandable distal tip aligns with the distal end of the outer catheter. The outer catheter can then be retracted relative to the clot retrieval catheter so that the self-expanding tip is uncovered and radially expands to deploy adjacent an obstructive thrombus. The profile of the tip can seal against the vessel wall proximal of the clot. This seals off vessel fluid proximal to the mouth and provides a large opening to easily receive the clot.

Another step can involve aspirating through one or both of the outer catheter and clot retrieval catheter to stimulate the thrombus into the mouth of the clot retrieval catheter. The captured thrombus can be aspirated through the lumen of the clot retrieval catheter and into the aspiration source and/or the clot retrieval catheter with the captured thrombus can be retrieved through the vasculature and out of the patient.

In another example, the method can further have the step of delivering a microcatheter across the target thrombus, while aspirating through the expanded tip of the aspirating clot retrieval catheter and deploying a mechanical thrombectomy device from the microcatheter. Once the thrombectomy device is deployed, the microcatheter can be withdrawn back along the path from which it was delivered to facilitate more efficient clot retrieval. The method can have the further step of retracting the thrombectomy device with the captured thrombus into the mouth of the aspirating clot retrieval catheter and withdrawing the clot retrieval catheter through the outer catheter and out of the patient.

In many cases, after retrieving some or all of the occlusive clot, contrast media can be injected through the outer catheter to allow a more thorough assessment of the degree to which the vessel is patent. Additional passes with the aspirating clot retrieval catheter and thrombectomy device can be made if an obstruction remains in the vessel. Any remaining devices can then be removed from the patient once adequate recanalization of the target vessel is observed.

Another advantage of using an expanding mouth clot retrieval catheter with an outer catheter is that once a captured clot has entered the distal end of the clot retrieval catheter, the clot retrieval catheter can be retracted through the outer catheter such that the outer catheter is left in place to maintain access at the target treatment location. While it is appreciated that certain clots may also require that the outer catheter be retracted with the inner clot retrieval catheter and clot, the majority of clots are likely to be removed through the inner clot retrieval catheter.

Further, when using a standard intermediate catheter, the lumen of the outer catheter may not be clean of debris, leading to a risk that during contrast injection potential thrombus remnants may be dislodged. To counteract this, a user of a traditional intermediate catheter can remove the catheter to flush any thrombus remnants outside of the body prior to injecting contrast, at the cost of losing access to the target treatment location. By comparison, the present disclosure provides means to minimize the number of catheter advancements required to treat a patient, thereby reducing the likelihood of vessel damage and the associated risk of vessel dissection in cases where multiple passes are required.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIG. 4A is a side view of an aspirating clot retrieval catheter, with a cutaway view of the expansile tip framework according to aspects of the present invention;

FIG. 4B is a view from the front of the expansile tip framework of the aspirating clot retrieval catheter of FIG. 4A according to aspects of the present invention;

FIG. 4C is a cross-section through the body of the aspirating clot retrieval catheter of FIG. 4A according to aspects of the present invention;

FIG. 5 is an enlarged view of the expansile tip framework of FIG. 4A as surrounded by the cover according to aspects of the present invention;

FIG. 6 is a view of the tapered proximal port of the aspirating clot retrieval catheter according to aspects of the present invention;

FIGS. 12A-12D are a series of views of another expansile tip framework according to aspects of the present invention;

FIGS. 13A-13D are a series of views of another expansile tip framework according to aspects of the present invention;

FIGS. 16A-16D are a series of views of another expansile tip framework according to aspects of the present invention;

FIGS. 17A-17D are a series of views of another expansile tip framework according to aspects of the present invention;

FIGS. 20A-20D are a series of views of another expansile tip framework according to aspects of the present invention;

FIGS. 21A-21D are a series of views of another expansile tip framework according to aspects of the present invention;

FIG. 24 is another illustration of an expansile tip aspirating clot retrieval system used in conjunction with a mechanical thrombectomy device, according to aspects of the present invention;

FIGS. 25A-25B are examples of possible flow restriction or sealing arrangements for directing aspiration in the system according to aspects of the present invention;

FIGS. 27-28 are flow diagrams outlining a method of use for the system according to aspects of the present invention.

DETAILED DESCRIPTION

The objective of the disclosed designs is to create a clot retrieval catheter capable of providing both local flow restriction/arrest with a large distal facing mouth and a tailored, highly flexible body section capable of navigating tortuous areas of the vasculature to reach an occlusive clot. Flow restriction and large tipped designs offer substantially greater aspiration efficiency. Such advantages can also be especially beneficial in the case of stroke intervention procedures, where vessels in the neurovascular bed are particularly small and circuitous, and as a result a tailored axial and bending stiffness profile can inhibit kinking and binding. The catheter can also be compatible with relatively low-profile access sheaths and outer catheters, so that a puncture wound in the patient's groin (in the case of femoral access) can be easily and reliably closed. The catheter can also feature internal and/or external low-friction liners, and an outer polymer jacket or membrane disposed around the support structure.

These improvements can lead to safe and more rapid access of a catheter and other devices to complex areas in order to remove occlusions and shorten procedure times. While the description is in many cases in the context of mechanical thrombectomy treatments, the systems and methods may be adapted for other procedures and in other body passageways as well.

Accessing the various vessels within the vascular system, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods of this invention in the description below, their function and exact constitution are not described in detail.

Figure 1:
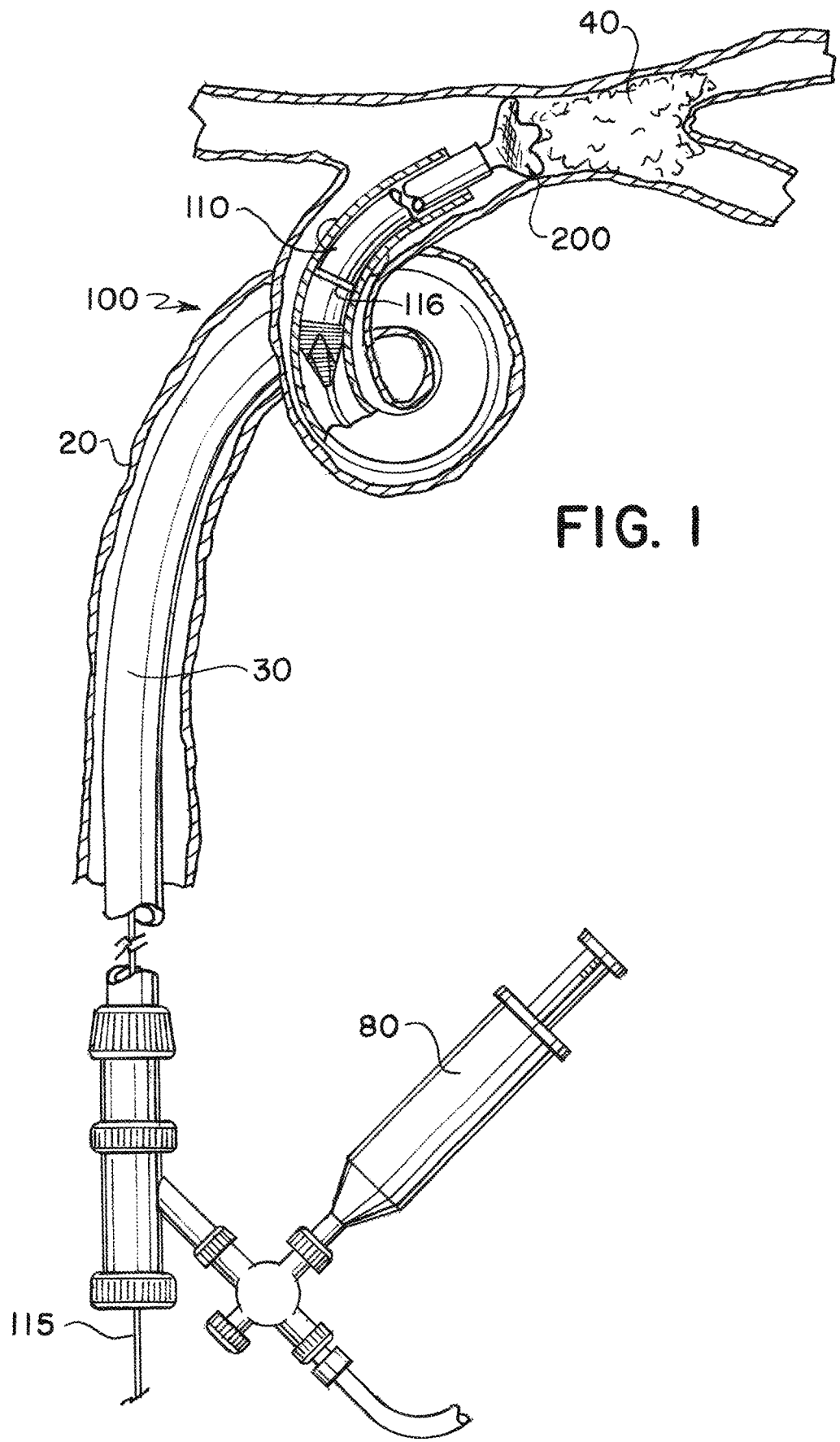
FIG. 1 is an illustration of an expansile tip aspirating clot retrieval system deployed to a target location, according to aspects of the present invention.
Figure 2:
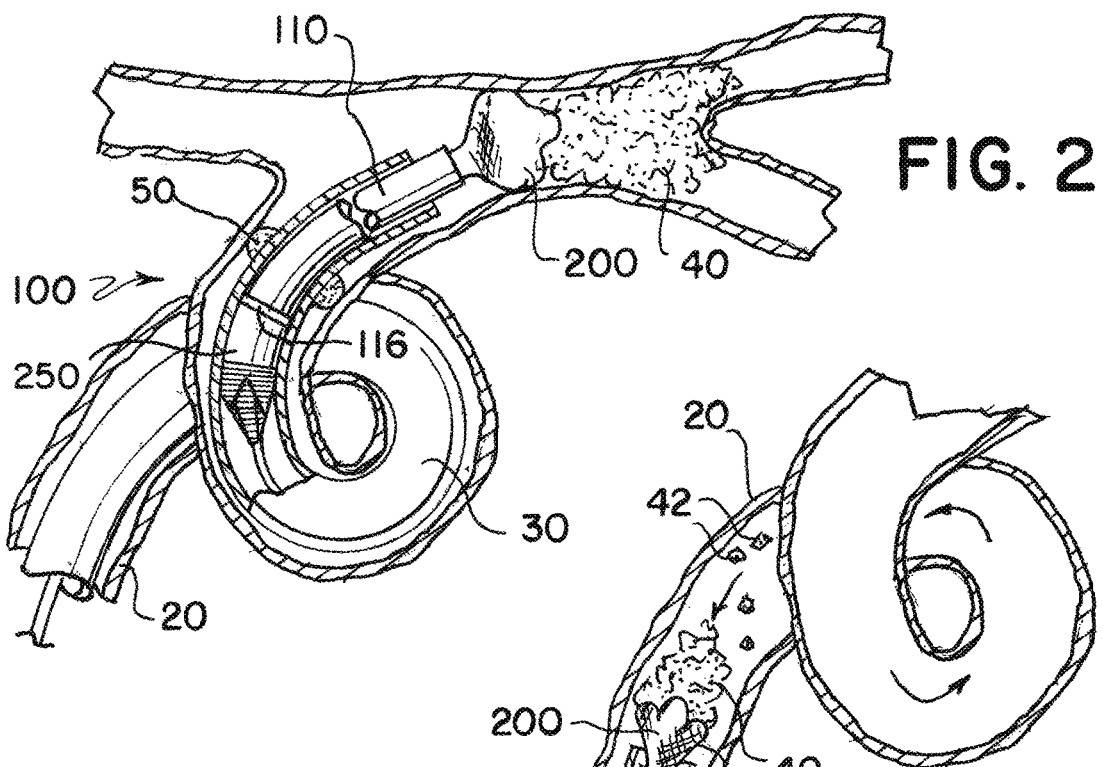
FIG. 2 shows another view of the system a target location according to aspects of the present invention.
Figure 3:
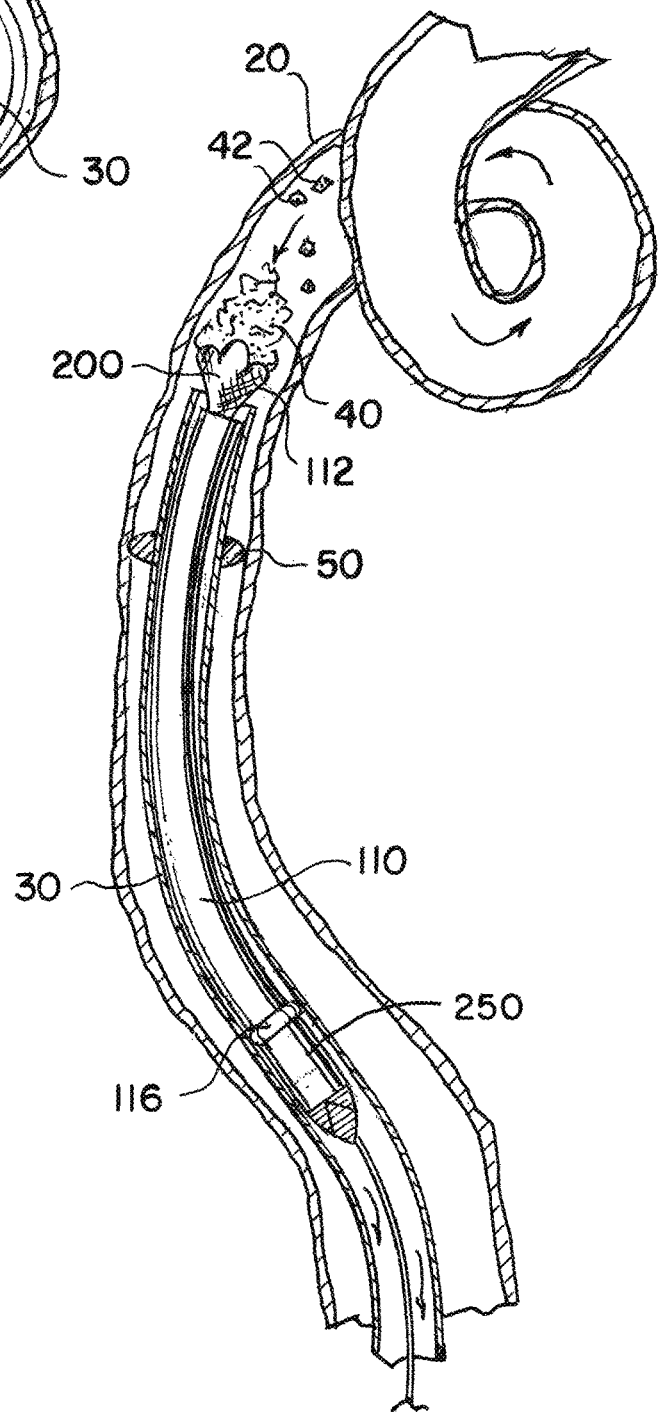
FIG. 3 shows a view of the system with captured clot being retrieved from the patient under aspiration according to aspects of the present invention.

Referring to the figures, in FIG. 1-3 there is illustrated a system 100 for removing an occlusive clot 40 from a vessel 20 of a patient. The system 100 can have an outer catheter 30 and an inner aspirating clot retrieval catheter 110. The clot retrieval catheter 110 can have an elongate proximal catheter shaft 115 for manipulating and delivering the retrieval catheter, and an expansile tip 200 at the distalmost end of the retrieval catheter. The expansile tip 200 can be sized and configured such that when deployed at the target site, it self-expands to atraumatically contact the inner vessel 20 walls to provide the maximum possible opening for aspirating and receiving the clot 40. The expanded tip can also arrest flow and prevent the unwanted aspiration of blood proximal to the tip.

The system 100 can enable a physician to use a standard sheath, guide, or outer catheter 30 to rapidly create a path and gain access to the vicinity of an occlusion, and then use an aspiration catheter 110 to aspirate the target clot 40. The aspiration catheter can be of traditional construction or can have rapid-exchange (RX) type features, many of which can greatly increase the speed and efficiency of the clot retrieval procedure.

In one example, the system can use an aspiration source 80 in conjunction with one or more flow restrictions or seals 50, 116. In many cases the expanded catheter tip can seal with the walls of the vessel, or the seal or seals can be selectively activated to project aspiration to the distal lumen of the aspirating clot retrieval catheter 110. The expansile tip provides a large mouth for efficient aspiration. The aspiration source 80 is first applied to the proximal lumen of the outer catheter 30 and then directed to the expansile tip 200 of the clot retrieval catheter 110. FIG. 3 shows one possible configuration for the retrieval step, where the outer catheter 30, clot retrieval catheter 110, and captured clot 40 are withdrawn from the target site. Seal 50 can arrest flow in the vessel and prevent any liberated clot debris 42 from migrating distally. Alternatively, instead of seal 116, a portion of the tubular catheter body can have a flared diameter to block the lumen between the two catheters. During retrieval, as the expansile tip 200 is drawn proximally and contacts the outer catheter 30, the tip 200 will seal off the space existing between the clot retrieval catheter 110 and the outer catheter. As the expansile tip 200 of the clot retrieval catheter 110 continues retraction proximally through the outer catheter 30, the tip can act as a piston to apply a further suction distal of the tip within the outer catheter until the tip exits the proximal end of the outer catheter 30.

The distal section of the aspiration clot retrieval catheter 110 has good thrust, trackability, and kink-resistant characteristics to aid in advancing it to the target location. It can therefore have multiple designs, or be fabricated from multiple materials, to give a reducing stiffness profile along the length to minimize insertion and retraction forces. Features can also be incorporated which bias bending about certain planes or encourage twisting to reduce the imparted strains. In this way the catheter will maintain excellent lateral flexibility but will not tend to expand or kink in compression.

As seen in FIG. 4A, the distal expansile tip 200 of the aspiration clot retrieval catheter 110 is intended to open up upon exiting the outer or intermediate catheter 30 in which it is delivered. The tip provides a large distal mouth 114 for aspirating the clot, sized to have an expanded size 125 nearly the same or just larger in diameter than the expected upper end of the target vessel diameter when unconstrained. When deployed, the tip can thus match the vessel diameter and have the radial pressure to seal with the vessel, or create enough of a flow restriction such that when aspiration is applied blood and the clot distal of the mouth will be drawn in to the catheter rather than blood proximal of the tip. If the expanded tip 200 does not seal, or forms only a partial seal, then the suction applied to the clot can be less effective as the flow will be directed proximal of the tip to an area which will likely be less restricted. However, a partially-sealing expansile tip 200 will still out-perform many current aspiration catheters that would leave more cross-sectional area open to the vessel proximal of the tip. An enlarged catheter body proximal segment 250 or seal 116 can also be used to occupy the lumen between the catheters.

In another example, the expansile tip 200 of the clot retrieval catheter 110 is designed to expand to a wide range of target vessel diameters, such as a carotid terminus (3.2-5.2 mm), a horizontal M1 segment of the Middle Cerebral Arteries (1.6-3.5 mm), and/or the Internal Carotid Artery (ICA, 2.7-7.5 mm). If the catheter is then retracted from an M1 segment to the ICA (or another route with a proximally increasing vessel inner diameter), the radial force of the self-expanding tip 200 will continue to seal with the vessel across a range of vessel sizes. Further, a tip capable of a range of target vessel diameters can also seal at vessel bifurcations which can have a wider cross-sectional area than the vessel proximal and vessels distal to the bifurcation.

The clot retrieval catheter 110 can have a proximal elongate catheter shaft 115 connected at the distal end to a proximal port 117. The clot retrieval catheter 110 can be delivered to the target site in the internal lumen 32 of the associated outer catheter 30. The clot retrieval catheter 110 can be manipulated by the shaft 115. The clot retrieval catheter 110 can be maneuvered independent of the outer catheter 30 by the physician, allowing the clot retrieval catheter to be retracted from the patient separately. Should the retrieval catheter become blocked by a thrombus, the outer catheter can be left in place to maintain access to the treatment location. Distal of shaft 115 the catheter body can be a support tube 124 structure disposed around a longitudinal axis 114 of the clot retrieval catheter 110. The support tube 124 can be fixedly connected distally to a strut framework 112 of the expansile tip 200.

At least portions of the framework 112 of the expansile tip 200 and the support tube 124 may be covered by a flexible cover 118. The expansile tip 200 can assume the expanded configuration by self-extending radially outward from the longitudinal axis 114 of the clot retrieval catheter 110 upon exiting the distal end 72 of the outer catheter 30. In one example, a highly elastic cover 118 stretches as the tip expands and can follow the contours of the underlying strut framework. In another example, the cover can be a fitted, non-compliant material which folds neatly when the tip 200 is collapsed back into the outer catheter 30. The cover can run the entire length of the support tube or it can terminate at or some distance distal to the proximal port 117.

The distal support tube 124 section of the clot retrieval catheter 110 can define an inner lumen 113 starting with a proximal port 117 and ending in a distal mouth 114 into which a clot can be retrieved. The lumen can be concentric with a longitudinal axis 111 of the catheter. An enlarged proximal segment 250 or a separate flow restrictor or seal 116 can be disposed around the outer circumference of the clot retrieval catheter to help translate aspiration to the target distal of the mouth. The preferred length 123 of the distal section of the catheter can depend somewhat on location of the target clot. Preferably, the tip 200 is expanded at the treatment location to avoid having to advance an expanded tip through the vasculature, allowing the length 123 of the tubular section to be relatively short. For clots located in the anterior or posterior cerebral arteries, the length 123 can be greater than 5 cm so that it can extend from the outer catheter right up to the proximal face of the clot, but less than 40 cm so that a minimal length can remain inside the distal end of the outer catheter while maximizing the afforded volume of the combined outer/retrieval catheter for aspiration. A shortened length 123 of the distal section also improves trackability and flexibility of the system to access targets. The shaft 115 material can have high tensile and compressive strengths, and the low profile of the shaft offers improved friction and pushability performance. The shaft 115 can be solid or can be a composite of multi-layer materials, such as a solid core and outer tubular portions (for example, a Nitinol core with an outer polymer jacket).

The large distal mouth 114 of the expansile tip framework 112 as shown from the front in FIG. 4B can offer improved performance over conventional fixed-mouth designs. Traditional fixed-mouth catheters can be hindered by having firm, fibrin-rich clots lodge in the tip and/or by having softer portions of the clot shear away. It is less likely for clots to become lodged in the tubular section of the disclosed expansile tip clot retrieval catheter 110 due to the progressive compression of the clot upon entry to the reducing funnel shape of the tip 200. Further, if a portion of the clot remains distal to the tubular section, the expansile tip 200 will be collapsed over the lodged clot to secure it and prevent it from becoming an embolus. The shape can be further collapsed as the tip is drawn back into the outer catheter 30 during or after a procedure to reduce or remove any flow restriction and allow blood and/or contrast to reach the distal vasculature.

Additionally, when aspirating through a traditional fixed-mouth catheter, a significant portion of the suction is directed to fluid proximal of the tip, reducing the suction directed to dislodge the clot and the success rate of clot removal. As the diameter of an expandable mouth catheter can be close to that of the vessel, clot shearing at the mouth of the catheter can be mitigated and the volume of fluid and clot distal of the mouth secured. By tapering down the diameter of the expansile tip 200 and/or support tube 124 the clot can be progressively compressed during retrieval so that it can be fully aspirated through the catheter.

FIG. 4C shows a cross-section view illustrating the various lumen of the system. The clot retrieval catheter 110 can be delivered through the lumen 32 of an outer catheter or sheath 30. The cover 118 can be disposed around ribs 122 of the support tube 124. One or more spines 120 can run the length of the support tube 124 and a large internal volume afforded to the lumen 32 for passage of ancillary devices.

The expanded tip 200 can assume a maximum radial size 125 larger than the diameter 119 of the outer catheter 30. and the tip mouth 114 can assume a maximum radial size of the expansile tip 200 when deployed. In this way, the tip can seal against the vessel 20 wall proximal of the clot 40. To maintain the seal, the radial force of the expanded tip must be high enough that the applied aspiration does not collapse the tip. The vacuum delivered through the outer catheter 30 to the clot retrieval catheter 110 can be a sufficient suction to draw the distal clot in to the mouth 114 of the tip, while preventing the unnecessary aspiration of blood proximal to the tip 200. This ensures that maximum suction power is transmitted and directed to clot disengagement from the vessel wall and retrieval through the catheter lumen 113. If the size of the clot 40 is too large to pass through the lumen 113 of the clot retrieval catheter 110, the expansile tip 200 can always be withdrawn in to the distal end 72 of the outer catheter 30 due to the smooth and tapered shape of the tip in the expanded condition.

A further detailed view of an example of the distal portion of the aspirating clot retrieval catheter of FIG. 4A is illustrated in FIG. 5. The expansile tip 200 can be designed such that in the expanded condition the tip framework 112 is roughly equal in size to or slightly larger than the inner diameter of the vessel 20 where the clot is located. Comparing the illustration seen in FIG. 3, the deployed expansile tip can be shaped such that the tip framework 112 has expanded to contact the vessel walls with a large and gentle radius. The flexible cover 118 can be a polymeric membrane disposed around the support tube 124 and is expanded to assume the profile of the tip framework 112 in the expanded state. The cover 118 can be trimmed to follow the contours of the tip mouth 114, can be folded over the tip framework 112, or can be left untrimmed.

In many examples, the expanded deployed form of the expansile tip framework 112 at the distal end of the clot retrieval catheter 110 can take on a flared or funnel shape. This shape allows a clot to be progressively compressed during retrieval to a smaller diameter so that it can be aspirated fully through the catheter an into an aspiration syringe or canister. If the clot does become lodged in the mouth 114 of the tip, the expanded mouth will protect the clot and prevent it from dislodging as the aspiration suction is maintained and the catheter 110 is retracted into the sheath or outer catheter 30, at which point the mouth will collapse over and grab or pinch the clot to pull it into the outer catheter.

The struts of the expansile tip framework 112 can be formed from Nitinol or another shape-memory material with sufficient elastic strain capacity such that the elastic limit would not be exceeded when the tip is constrained and delivered in the collapsed configuration within an outer catheter. This elastic strain capacity allows the tip to be effectively spring-loaded so that the tip can self-expand when deployed out of the distal end of the outer catheter. In another case, the framework can be constructed from wire, allowing a non-superelastic material like a stainless-steel alloy to be employed, since the wires would be free to move independent of one another. It is appreciated that a framework 112 constructed of wire using superelastic or shape memory materials can also be envisaged, such a device offering improved torque and durability characteristics. In another case, a framework 112 can be laser cut from a non-superelastic material that accommodates strain by including cells or bends, with a lower degree of strain required to move from a collapsed state for delivery to an expanded state for clot retrieval. For example, the framework can include additional cells, longer cell struts, and/or lower cell angles to reduce strain requirements.

As seen in FIG. 6, the proximal port 117 can serve as a tapering transition between the shaft 115 and the main catheter body and can also form the entrance to the lumen 113 of the catheter 110 for other devices to be used during the procedure, such as a guidewire, microcatheter, thrombectomy device, or angioplasty balloon. To facilitate the introduction of other devices, the port 117 can have an axially-tapering profile over a transition length 129 from the shaft to the body to prevent other devices from snagging at the transition. The shaft 115 can overlap a portion of a spine 120 of the catheter support tube 124 and be locked together by mechanical features or with an overlaid reinforcing polymer jacket.

The catheter support tube 124 can also be laser cut from a hypotube or be of otherwise similar construction, including braids with overlaid or interwoven spine(s), enabling good push and torque characteristics, small bend radii, kink resistance, and solid resistance to tensile elongation. Commonly used materials include Nitinol and familiar medical-grade stainless-steel alloys like 304 and 316. When a cut hypotube is utilized, the expanding mouth support framework 112 can be formed integral with the hypotube such that the stiffness profile of the catheter is smoother and weak transitions can be eliminated. The hypotube can be further coated with a low-friction sleeve or jacket, such as PTFE, high-density polyethylene, or a similar fluoropolymer. Hypotubes of different materials, such as stainless-steel for a proximal section and Nitinol for a distal section of the tubular support tube, can also be used and joined by welding, bonding, or by holding interlocking features in place with inner and/or outer polymer jacket materials.

Figure 7:
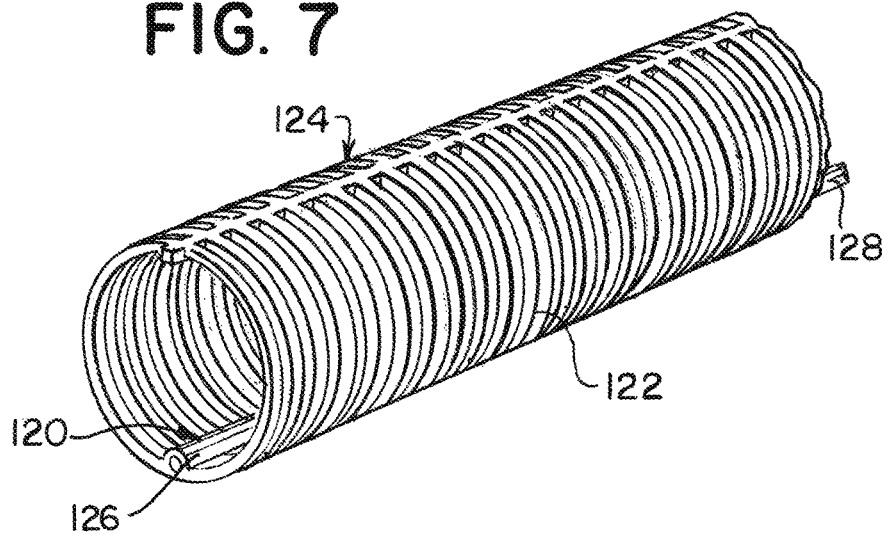
FIG. 7 is an isometric view of a support tube according to aspects of the present invention.

The support tube 124 of the clot retrieval catheter 110 can have a structure similar to that illustrated in FIG. 7. The framework can have one or more axial spines 120 extending distally from a proximal end 128 to a distal end 126, The spine can be of tubular or wire construction such that is has good axial stiffness for advancing and retracting the catheter while having excellent lateral flexibility for navigating within bends in the vasculature. The use of multiple spines encourages flexing along defined planes and while reducing the possibility of the support tube 124 elongating under tensile loads, such as when the expansile tip is withdrawn in to the mouth of the outer catheter. Running the length of the axial spine or spines can be a plurality of loop ribs 122 which can be axisymmetric with the longitudinal axis 111 of the clot retrieval catheter 110. The loop ribs 122 can be a simple circular configuration as shown or take a more complex shape as required.

In one case, the axial spine 120 and loop ribs 122 can be cut from a single hypotube, where the individual ribs can be formed by cutting slots using laser machining or electrochemical means. In another case, the loop ribs can include interlocking spirals, a helical, or a continuous hinged configuration. By utilizing a spine 120 and rib 122 configuration, the size and shape of the spine can be customized along with the density and size of the rib struts, yielding greater flexibility to certain portions of the catheter. This is important for situations where the system must be advanced from a patient's inner thigh, over the cardiac arch, and up into the intracranial vessels inside the patient's skull and thus the distance and tortuosity can be significant.

The interior of the loop ribs can define the inner lumen 113 of the clot retrieval catheter 110. The cover 118 can be disposed around the supporting ribs and fused or stretched in place. The axial spacing of the ribs can be dense enough to maintain column strength and provide support for and prevent collapse of the cover but also distant enough to provide good deliverability properties to the distal section of the catheter. In situations where the clot retrieval catheter has an inflatable seal 116, an internal lumen 121 can be supplied within an axial spine 120 for independent actuation of the seal. In another example, a polymeric low-friction liner is applied to the inner surfaces of the clot retrieval catheter 110, with the loop ribs 122 and spines 120 being sandwiched between the liner and the outer cover. The outer cover may be supplied in a longitudinal series and/or radial layers of differing materials to further tune the stiffness at different points along the length of the catheter.

The tubular body of the aspirating clot retrieval catheter 110 can also be made solely from a polymer tube that may or may not have multiple layers. The surfaces of the polymeric tube can be profiled with a series of ridges and recesses that afford enhanced torque, push, and trackability characteristics. In one example, the ridges and recesses are applied by passing the polymeric tube section through a heated profiling die that melts and cools the tube as it is passed through in various directions.

The ideal nominal diameter of the catheter 110 depends on the location of the target clot and the diameter of the outer catheter 30 through which the catheter is to be delivered. For retrieval of clots in the intracranial vessels of the cerebral vascular bed, where vessel diameters at the M1 locations are commonly around 3 mm, an applicable system might have an outer catheter with an inner diameter of 0.065" to 0.080" and an RX clot retrieval catheter with an inner diameter of 0.055"-0.070". Upon deployment from the outer catheter, the maximum diameter 125 of the expansile tip can be a minimum of 3 mm (but in some instances up to 6-7 mm), allowing it to seal against the walls of the vessel and providing a distal mouth as large as the vessel itself. In some instances, the tip 200 can also provide an opening large enough to oppose bifurcations and/or proximal vessel locations. This seal, in combination with a maximized proximal lumen of the disclosed RX system over a conventional catheter, offers benefits in terms of aspiration force at the face of the clot and increased flowrates with a design that utilizes the larger inner diameter of the outer catheter. The outer catheter 30 restrains the funnel in a collapsed configuration to facilitate advancement to the intended deployment location. When the funnel is designed in a manner that allows distal advancement of the expanded mouth within a blood vessel, for example from a balloon or long sheath guide catheter located in the ICA to a target treatment location such as the M1 or M2 vessels, a balloon guide can serve as a larger proximal lumen offering an inner diameter in the range of 0.085" to 0.100", thereby greatly increasing the flowrate directed to the treatment location. With a conventional system, the aspirating catheter must always have a diameter significantly less than that of the balloon or long guide sheath catheter in which it is positioned, limiting the efficacy of the applied vacuum by not employing the larger lumen of the outer catheter.

It can be expected, however, that procedural challenges may sometimes dictate the practical size of the expansile tip 200. For example, for deliverability the expanded diameter 125 of the expansile tip may be slightly smaller than that of the target vessel in situations where a lower profile catheter is a higher priority than a sound seal between the tip and the vessel walls.

It can be envisaged that the pattern of the framework 112 struts of the expansile tip 200 can take many forms. In one example, the layout of the tip pattern is laser cut from a Nitinol sheet or tube and has a series of interconnected struts, as illustrated by the flattened plan view in FIG. 8 At the proximal end 213 of the tip framework, a base 216 of the framework 112 can be connected to a spine 120 or spines of the support tube 124 by one or more struts forming axial ligaments 218. The axial ligaments 218 can also connect to a point or points on the circumference of the most distal loop rib. The axial ligaments can be parallel to the central longitudinal axis 111 of the aspirating clot retrieval catheter 110. In another example, the support tube 124 can be monolithically formed with the expansile tip framework 112 such that the axial ligaments 218 transition to support arms of the tip as a distal continuation of the axial spine 120.

One or more link members 214 can project distally from the tip base 216. Each link member 214 can terminate at the convergence of two or more proximal support arms 212 to form a closed cell. In one example, link members 214 can have a broad and curvilinear form, which gives added flexibility to the framework and allows the member to lengthen in order to reduce the likelihood of the ribs 122 of the support tube 124 pulling the mouth of the expanded tip framework 112 proximally during retraction of a clot under aspiration where link members 214 are not in line with a spine(s) 120 of the support tube. Keeping spines 120 of the support tube 124 in line with link members 214 and/or support arms 212 allows direct transmission of push/pull forces between said members and can offer the most efficient resistance to elongation while the device is being advanced or retracted in a vessel or outer sheath. In another example, there are no link members and the support arms themselves are directly connected to the tip base or the most distal loop rib. The support arms 212 can be connected distally at proximal crown troughs 215 by curved crowns or undulating tip segments 210, which form the perimeter of the mouth 114 of the expansile tip framework 112. The crowns 210 can have a distally convex curvature extending from where the tip segments meet adjacent segments at the proximal crown troughs 215. Together, the crown struts 210 and adjoined support arms 212 can form closed cells which may give the distal portion of the expansile tip 200 a petal-like appearance with rounded edges. These cells are spaced around the circumference of the tip, and the cells form the terminal end of the tapered shape with an atraumatic large, flared radius of curvature for navigating and interfacing with the vasculature and ensuring good contact with a clot.

Figure 8:
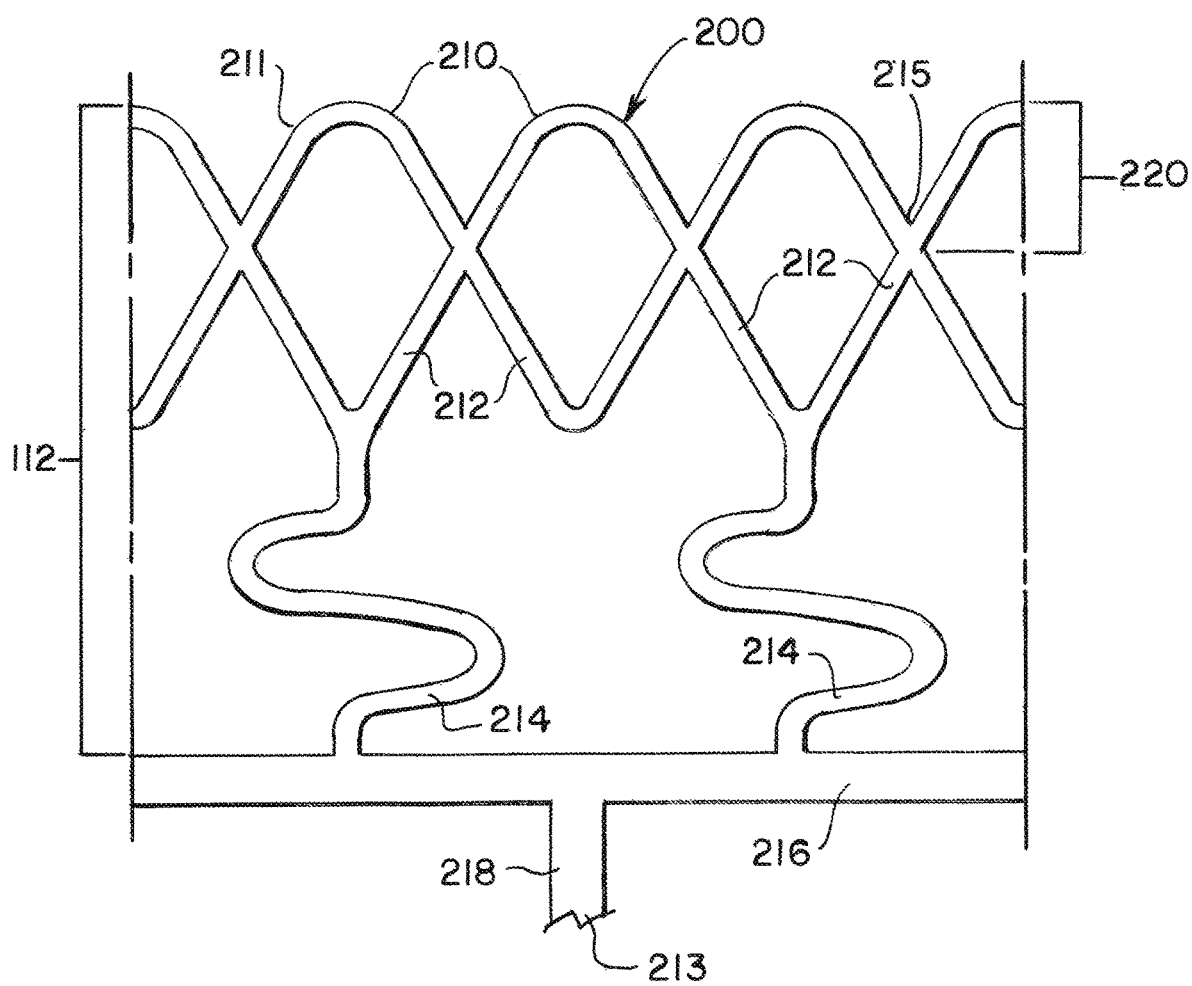
FIG. 8 is a plan view of the expansile tip framework of FIG. 4A according to aspects of the present invention.

Of course, the tip framework structure 112 and patterns shown in FIG. 8 and other figures discussed herein are used to illustrate single aspects of the present invention. The present invention can have tip frameworks of a variety of shapes and sizes and can be made from a single section or from multiple sections.

When in the expanded state, at least part of the tip 200 may taper distally from a larger radial dimension to a smaller radial dimension. In this configuration, the outer axial profile of the tip body can also be rounded to provide a smooth interface with the vessel wall. By combining rounded crown features with a rounded outer axial profile that tapers radially inwardly in a distal direction (from the maximum radial dimension at an intermediate location to a diameter that is greater than the support tube but less than the maximum diameter) and including link members 214 and/or support arms 212 that taper from the support tube 124 to the maximum diameter in a shallow angle, preferably less than 45 degrees and more preferably less than 30 degrees, the expanded tip 200 can be advanced distally within a vessel in an atraumatic manner that does not pose a risk of damage to the vessel wall.

The framework 112 of the expansile tip 200 can be overlaid by a flexible cover 118 as seen in previous figures. Various features, such as the curvilinear profile of the link segments 214 and the broad petal-shaped cells formed by the crowns 210 and the support arms 212 of the pattern in FIG. 8, combine to provide more supporting surface area to buttress the cover. When the expansile tip is fully deployed, the cover surface on the tip can taper to an increased diameter in a curved, funnel-like profile until it is largely parallel with the longitudinal axis 114 at some point approximate the distal end 211 of the tip.

Figure 9A:
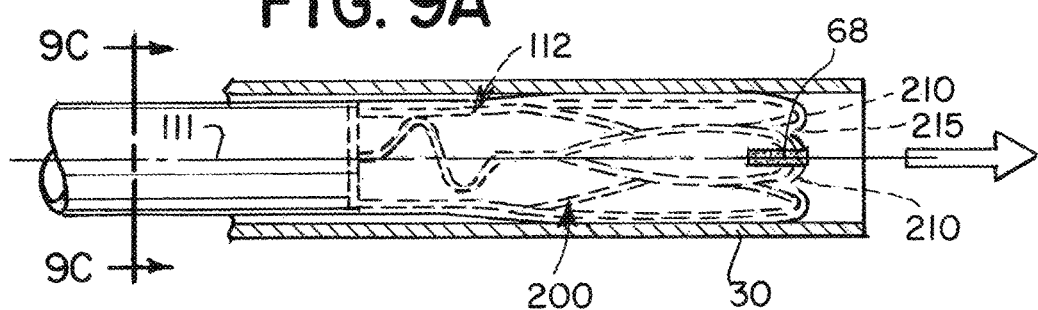
FIG. 9A is a view of the collapsed delivery configuration of the expansile tip of FIG. 5 according to aspects of the present invention.
Figure 9B:
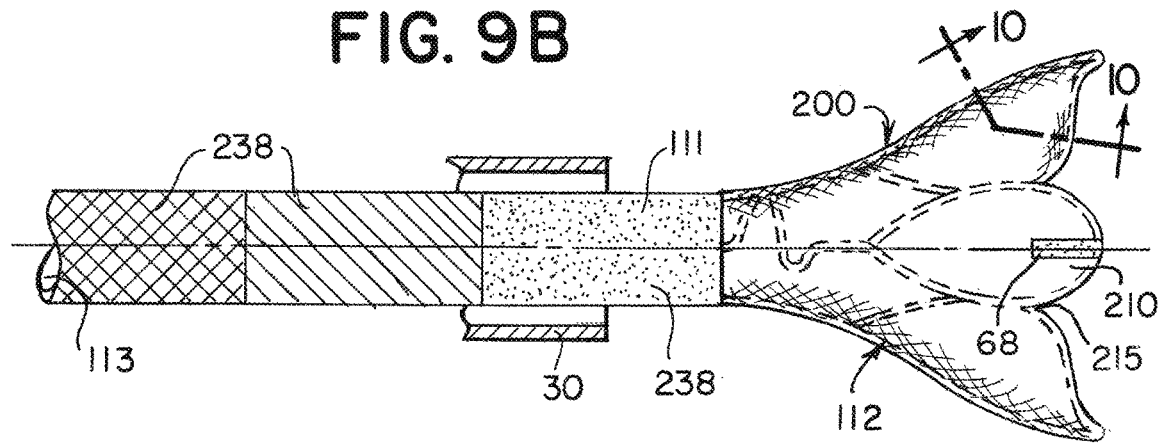
FIG. 9B shows the expanded deployed configuration of the expansile tip of FIG. 5 according to aspects of the present invention.

The collapsed delivery configuration and expanded deployed configuration for one example of the expansile tip 200 are shown in FIG. 9A and FIG. 9B, respectively. When in the collapsed state constrained within the outer catheter 30 in FIG. 9A, the petal-shaped cells formed by the crowns 210 and the support arms 212 fold in a necked-down and largely axisymmetric fashion about the longitudinal axis 111 hinging at the proximal crown troughs 215, and at least a length of the expansile tip 200 between the proximal end 213 and the distal end 211 can share a common first radial dimension with the outer catheter 30. This first radial dimension is less than a maximum second radial dimension of the tip in the expanded state. An expanded second radial dimension 125 can be equal to or larger than the diametric size of the target blood vessel when unconstrained. Upon clearing the distal end of the outer catheter, the expansile tip framework 112 can project radially outward and pushes the cover 118 to the deployed shape, as shown in FIG. 9B. The petal-shaped cells open hinging about the proximal crown troughs 215 to assume a maximum radial size approximate the distal end 211 of the expansile tip 200.

Visibility during deployment of the aspirating clot retrieval catheter 110, as well as the location of the catheter and clot 40 during capture and retraction can be aided by adding alloying elements (such as palladium, platinum, gold, etc.), by the application of a radiopaque compound, or through the placement of radiopaque markers 68 on one or more of the catheters and devices. Suitable practices are frequently used in connection with other devices and implants and are well known in the art. For example, a radiopaque compound can be incorporated on the cover 118 around the expansile tip 200, or one or more radiopaque markers 68 can be added near the distal end 211 of the tip, as seen in FIGS. 9A-9B. By incorporating multiple markers 68 at positions close to the portion of the tip 200 that reaches maximum diameter when expanded, the physician will be able to visually confirm that the mouth has fully expanded to the vessel wall. Additional markers may be placed at the base of the expanding mouth and/or at a more proximal position so that the physician can visualize the curvature of the device when deployed and either advanced or retract slightly to adjust the curvature to achieve a straighter axial profile that can be more desirable for aspirating a clot into the distal end of the device. Further, markers can be placed on the other devices, such as microcatheters and auxiliary mechanical thrombectomy devices where used to mark for the physician the terminal ends of the devices during the procedure. Markers can also be used to indicate the working lengths and expanded diameters of stentrievers. Such markers would be particularly useful if such devices were not completely withdrawn into the outer catheter 30 during retraction from the target site and to fine tune positioning between devices relative to the target clot.

The cover 118 can take a variety of different forms or configurations as further described herein. The cover can be formed in a collapsed, substantially tubular profile with a highly elastic material such that the expanding of the expansile tip will impart a sufficient radial force to stretch the tubular structure to the profile of the expansile tip when unconstrained. Alternately, the cover 118 can be formed in the expanded state of the expansile tip 200 such that it can be folded or creased into the collapsed state when in an outer catheter. If the support tube 124 and tip framework 112 are cut from a hypotube, spaces, slots, or patterns can be laser-cut into the outer surface of the hypotube the cover can be reflowed or injection molded into the spaces during manufacturing. The cover 118 can also be adhered to the struts of the support tube 124 and tip framework 112 using heat or an adhesive with a primer.

The cover 118 can be of a construction where it has good ductility and a high elastic strain limit so that it can be easily expanded by minimal radial forces from the underlying self-expanding frame 112. Or, if the cover 118 is formed in the expanded configuration with an elastomeric or non-compliant material, it can be capable of wrapping down neatly when collapsed for delivery and recovering when expanded for use. The cover of the tip framework 112 can also have flow directing features, such as a plurality of flexible fins or vanes (not illustrated), disposed around the inner circumference in a configuration that entrains vortex or laminar flow. Such features can be included in a forming or molding mandrel.

The cover 118 can be trimmed to follow the contours of the strut framework 112 along the perimeter of the mouth 114 or it can be finished with a planar face. In another example, the cover membrane can be folded radially inward to a position proximal of the mouth 114 and heat welded between the inner and outer layers. The thickness of the cover 118 can be maintained between and over the struts of the strut framework 112, it can be finished with a uniform thickness, or it can vary in thickness between the base and distal tip of the expanded tip 200.

Figure 9C:
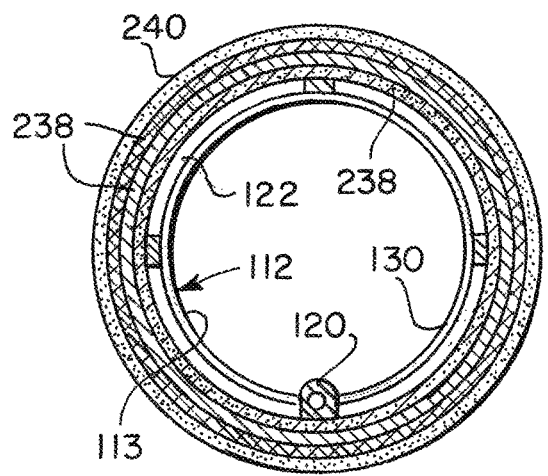
FIG. 9C is a cross-section of the catheter of FIG. 9A with a series of radial polymer jackets according to aspects of the present invention.

A single or variable stiffness cover 118 can be extruded over the support tube. Alternatively, the cover can be a formed from a series of polymer jackets 238. Different jackets or sets of jackets 238 can be disposed around the loop ribs 122 at discrete lengths along the axis of the support tube in order to give distinct pushability and flexibility characteristics to different sections of the tubular portion of the catheter as shown in FIG. 9B. By configuring the jackets in an axial series, it is possible to transition the overall stiffness of the catheter from being stiffer at the proximal end to extremely flexible at the distal end. Transitions between jackets 238 can be tapered or slotted to give a more seamless transition between flexibility profile of abutting jackets in longitudinal series. Alternately, the polymer jackets 238 of the cover can be in a radial series disposed about the support tube in order to tailor the material properties through the thickness, as shown in FIG. 9C.

The series of polymer jackets 238 can be butted together over the support tube 124 framework and reflowed using heat to fuse the jackets sections to each other and to the framework. The expansile tip framework 112 can have the same or a separate jacket or jackets that can be dip coated and can butt against, extend to, or be situated under or over the jacket or jackets of the support tube. If the jacket of the tip framework 112 rests under the jackets of the support tube 124, it can be manufactured from a material capable of withstanding the heat generated when the jackets of the support tube are reflowed. Alternately, if desired that the jacket of the tip framework be made with a material less resistant to the heat generated during reflow, a heat shield and/or precision laser reflow machine can be used to protect the tip framework cover. The jackets and cover sections can also be made from similar or compatible materials that can bond to each other during reflow. A cover with a single outer jacket can also be pre-formed with variable stiffness and elasticity characteristics and substituted for the series of polymer jackets, for example by extruding a variable blend of polymers with different stiffness characteristics.

In another example, the tip framework 112 can include an electro-spun or other porous cover that allows for reduced blood flow from the proximal side of the tip-vessel wall seal. A flow reduction between 50% to 99%, more preferably from 60% to 80%, will still direct most of the aspiration flow to the clot while allowing for a small restoring flow portion from the proximal side. This flow can help to reduce the possibility of vessel collapse under excessive aspiration, in locations where vessels have little support from surrounding tissue, or in cases where there are no side branches between a blocked vessel and the expanded tip 200 and a mechanical thrombectomy device or stentriever has not been able to open a portion of the blocked vessel.

Figure 10:
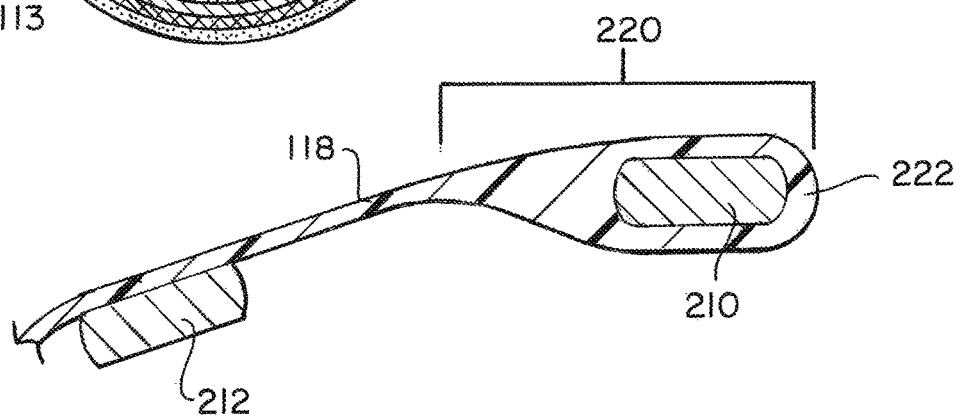
FIG. 10 shows a cross-section view of an elastomeric lip of the expansile tip according to aspects of the present invention.
Figure 11A:
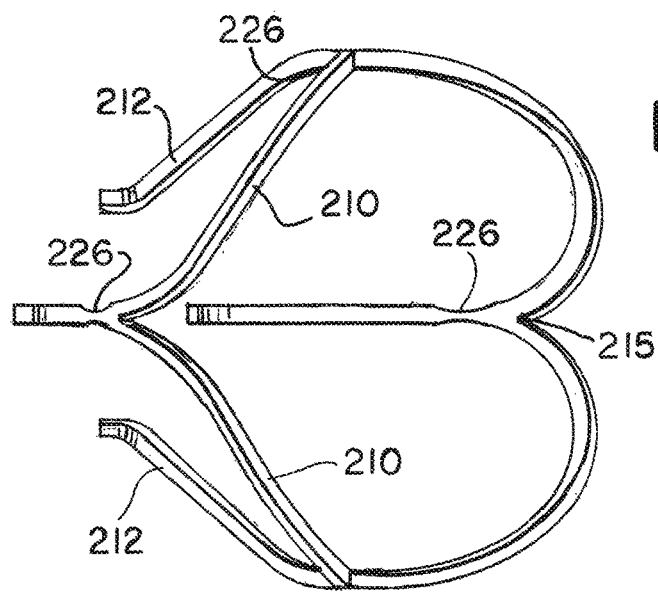
FIGS. 11A-11D are a series of views of an expansile tip framework according to aspects of the present invention.
Figure 11B:
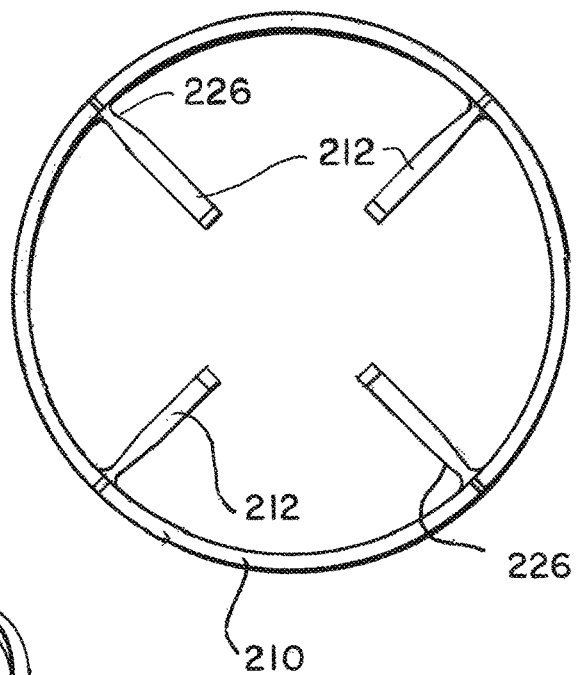
Figure 11C:
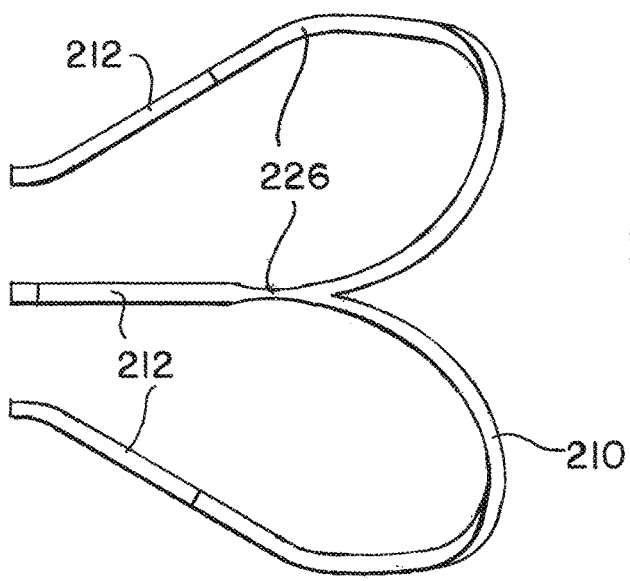
Figure 11D:
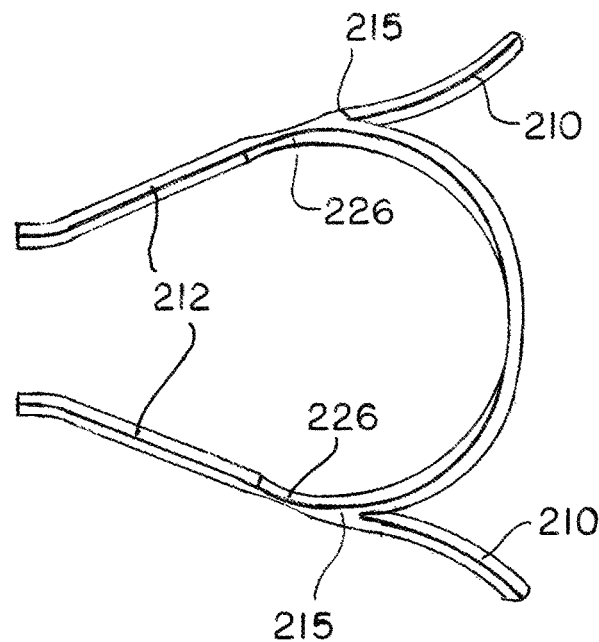
Figure 12A:
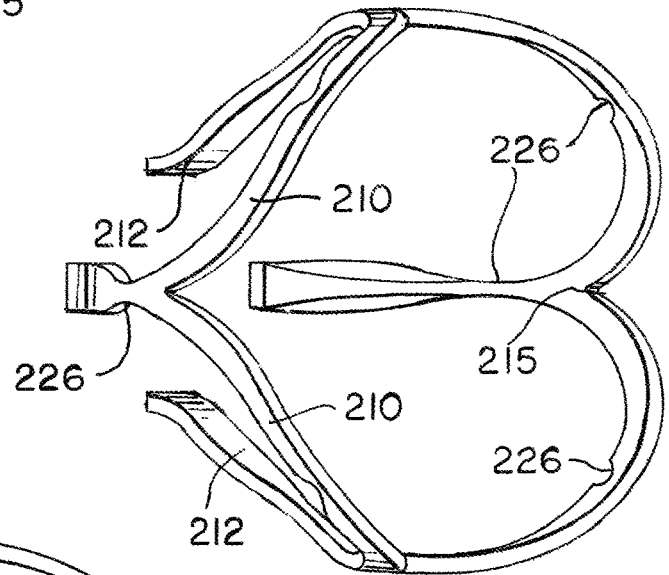
Figure 12B:
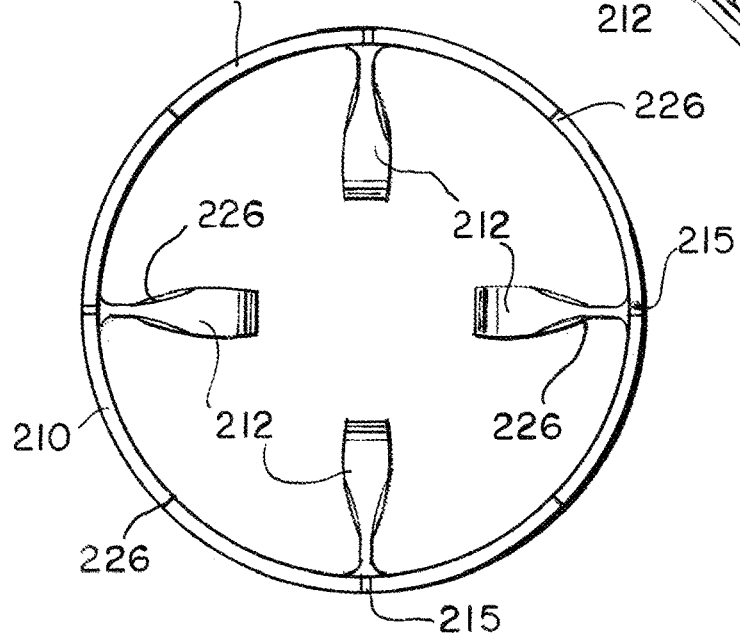

Additional steps can be taken to make a seal with the target vessel more atraumatic. In addition to or in place of a cover 118, a length of the tip extending proximal from the distal end 211 can define a dip zone 220 which designates the portion of the tip which can be further dip coated with a low-friction elastomer, as shown in FIG. 10. The struts near the distal end 211 of the expansile tip framework 112, such as the crowns 210 and the support arms 212, serve as the substrate for this process. Dip coating can be a reliable process for coating complex geometries. The dip coating deposits a seamless, circumferential, and atraumatic elastomeric lip 222 around and overhanging the crowns 210. This overhang of the lip can also resist a captured clot from backing out of, and potentially migrating distal to, the clot retrieval catheter. The dip zone can also further extend to a proximal length of the connecting arms 212 or even the entire tip framework 112 as defined by the longitudinal span of the dip zone 220.

In order to dip coat and form the lip over the expandable mouth of the catheter, a substantially conical mandrel matching the undulations of the tip framework can be placed on the interior aligned with the shape of the framework. Multiple dip coated layer can be applied before and/or after removal of the mandrel. Post-mandrel removal, dip coating will allow a portion of the lip to form radially inward and outward of the tip framework to overhang the edges. Alternately, the dip coating mandrel can have machined features such as a circumferential recess or grooves that allow material to form under the tip ends. Other features, such as longitudinal, axial, or offset patterns can be machined in to the mandrel so that these features are imprinted to the cover during dipping to achieve a cover with additional support and/or flexibility in certain locations.

The final state of the entrained material of the elastomeric lip 222 can be tuned by adjusting the controlled factors of the dip coating process. Elements such as submersion dwell time, substrate withdrawal speed, temperature, humidity, and number of dipping cycles can all be modified to give the lip a desired soft and uniform profile.

In another example, the lip 222 can be formed by a loose or baggy membrane cover 118 that is placed over the mouth of the tip framework 112 and folded radially inward. The overlapping layers can be heat welded in place so that the membrane extends radially outward and radially inward of the circumference of at least a distal portion of the expanding tip framework defined by the dip zone 220.

The elastomeric lip 222 creates a gentle contact surface for sealing against the walls of the vessel 20 when the expansile tip 200 is deployed to the expanded configuration. As formed, the lip can be a soft elastomeric, gel, and/or hydroscopic rib to provide atraumatic contact with the vessel wall. The seal can focus the suction distally and restrict the flow of fluid proximal of the tip, where there is no clot, from being drawn in to the catheter.

In the aforementioned examples, a low-friction inner liner 130 as applied to the inner circumference of the support tube 124 is shown in FIG. 9C. An inner liner, such as PTFE can offer the advantage of reducing friction with ancillary devices that are being advanced through the lumen 113 of the catheter. The liner material can also extend to an outer surface of the support tube, an intermediate position within the inner diameter and outer diameter of the support tube 124 or it may only be bonded to the surface of the inner diameter of the support tube. Having a liner which is bonded only to the inner diameter of the support tube will allow the rib struts of the support tube to bend more freely, since a liner extending more radially outward relative to the wall thickness of the support tube can stiffen the catheter. It is also possible to have a liner fused to the inner diameter surface of the support tube 124 and also have a cover 118 or membrane connected to the outer diameter surface, with gaps between support tube ribs 122 so the ribs are free to move axially. In another example, the cover and/or liner can be sprayed or dip coated such that the surface of the cover and/or liner can undulate with that of the support tube 124.

An inner liner can add stiffness to the catheter and has the potential to delaminate, while an outer coating or multiple coatings can blister or flake off in tortuous bends. As an alternative, the cover 118 can be one or more outer jackets impregnated with or formed from a polymer containing low-friction particles 240 to decrease the coefficient of friction of the outer and/or surfaces to allow for smooth delivery through the outer catheter. Such a material can eliminate the need for an internal liner and an outer lubricious coating, as the particles in the material will move to the outer and inner surfaces to provide low-friction characteristics. Eliminating the inner liner and outer lubricious coating can improve the durability and flexibility of the device. In another example, the inner and/or outer surfaces can be modified with methods such as ion implantation or plasma to impart low-friction properties.

In addition to those already described, further examples of expansile tip 200 profiles and structures are illustrated in FIGS. 11-22. Referring to FIGS. 11A-D, an expansile tip framework 112 can have four crowns 210 jointed at proximal crown troughs 215 and four support arms 212 having two sets of opposing arms. Each support arms can attach proximally to a base or to the distalmost rib of the support tube 124. The support arms are not connected to one another, so they are free to move and flex independently. The support arms can have narrowed sections or segments 226 to enhance flexibility for delivery. The narrowed segments can be circumferentially aligned or circumferentially offset. For example, two sets of opposing support arms can have circumferentially-aligned narrowed segments that would allow the framework to have flexibility in two planes perpendicular to each other and to bend at two locations that are longitudinally apart. In another example, the support arms 212 can have more than one narrowed segment 226. Additional narrowed segments 226 would reduce the radial force of the expanded tip compared to support arms with only one narrowed segment, so long as the support frameworks 112 have sufficient hoop strength to withstand the pressure gradient created when aspiration is applied.

In another example shown in FIGS. 12A-D, a tip framework 112 with four crowns 210 and four support arms 212 can have narrowed segments 226 on both the support arms and crown struts to allow the framework to bend more easily during advancement and to aid in easily collapsing the frame when it is withdrawn in to the mouth of an outer or intermediate catheter. The struts of the crowns and support arms can also be made wider in some areas to increase the radial force of the expanded tip while maintaining a low profile. The support arms can neck down into narrowed segments proximal of the proximal crown troughs 215 and then flare out to a wider section near the proximal end of the tip framework.

In FIGS. 13A-D there is shown a tip framework 112 with six crowns 210 joined to six support arms 212 at proximal crown troughs 215. Each of the support arms can have a narrowed segment 226 offset a longitudinal distance from the crown troughs 215. The proximal ends of the support arms can be formed integrally with a tubular support tube 124, and connect to a tip base 216, an axial spine 120, or the distalmost loop rib 122. Having support arms 212 which each connect independently with the support tube 124 yields increased flexibility around the circumference, allowing the tip framework 112 to better conform to vessel anatomy.

Figure 14A:
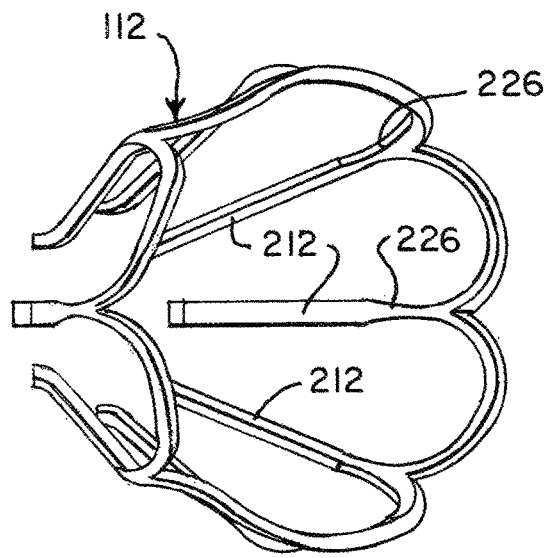
FIGS. 14A-14C are a series of views of another expansile tip framework according to aspects of the present invention.
Figure 14B:
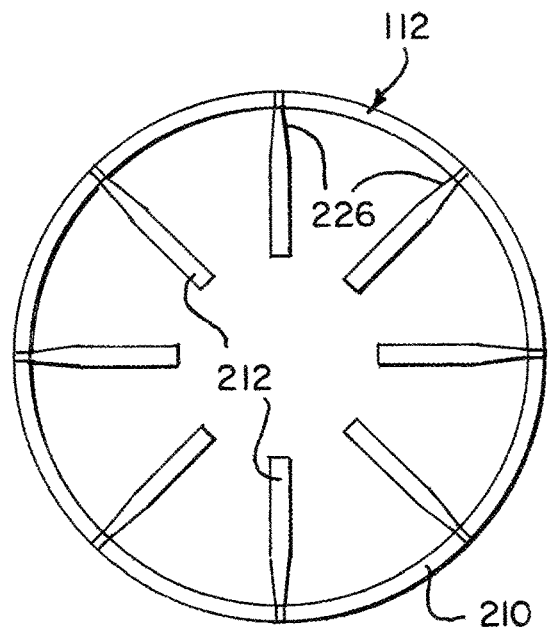
Figure 14C:
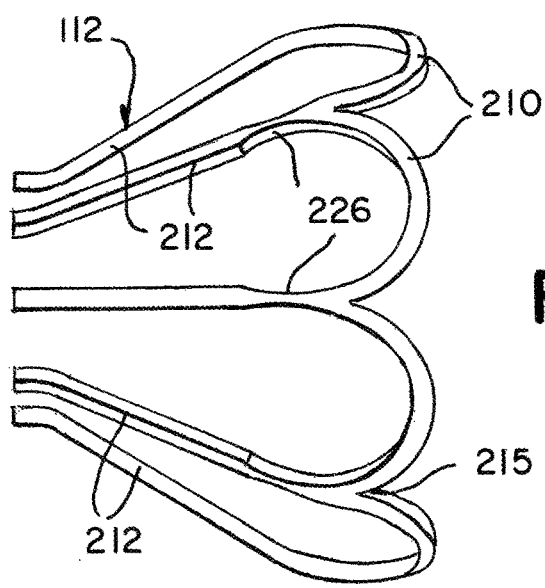

FIGS. 14A-C illustrates several views of an example where a tip framework 112 has eight crowns 210 and eight support arms 212. Compared to examples with fewer crowns, additional crowns and support arms sacrifice some framework flexibility while providing additional support for the cover 118. The cover can either follow the contours of, or be stretched over, the crowns and support arms. Similar to other examples, the support arms and/or crowns can have narrowed segments 226 for additional flexibility.

Figure 15A:
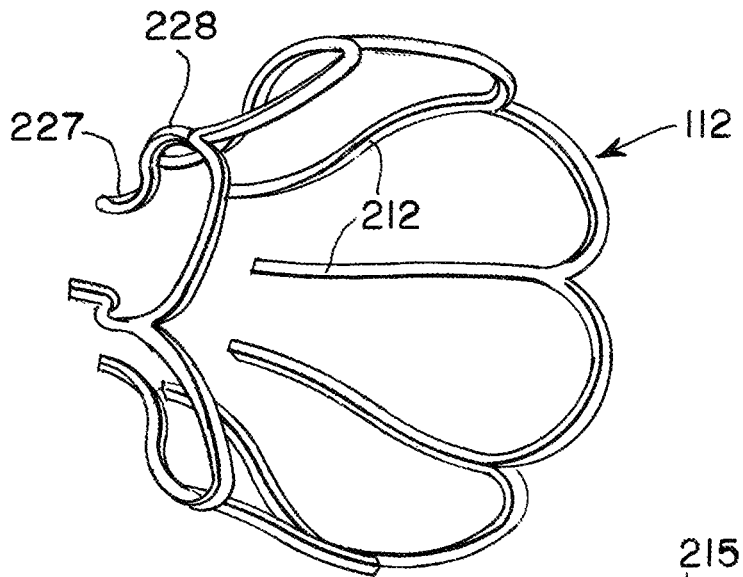
FIGS. 15A-15C are a series of views of another expansile tip framework according to aspects of the present invention.
Figure 15B:
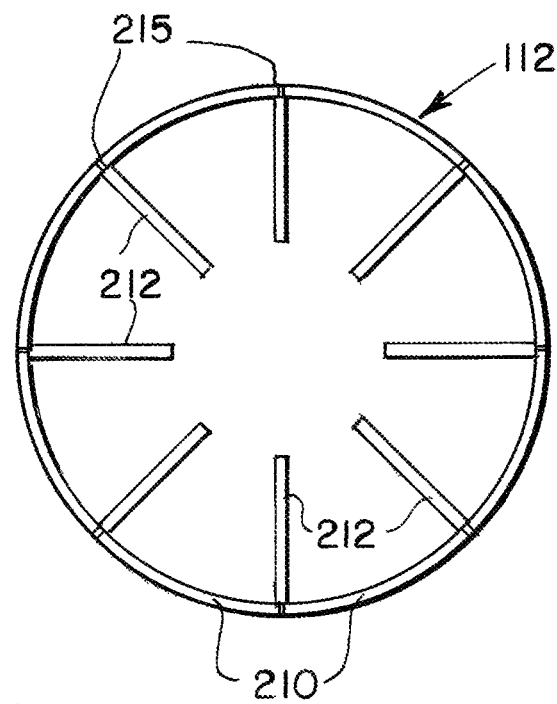
Figure 15C:
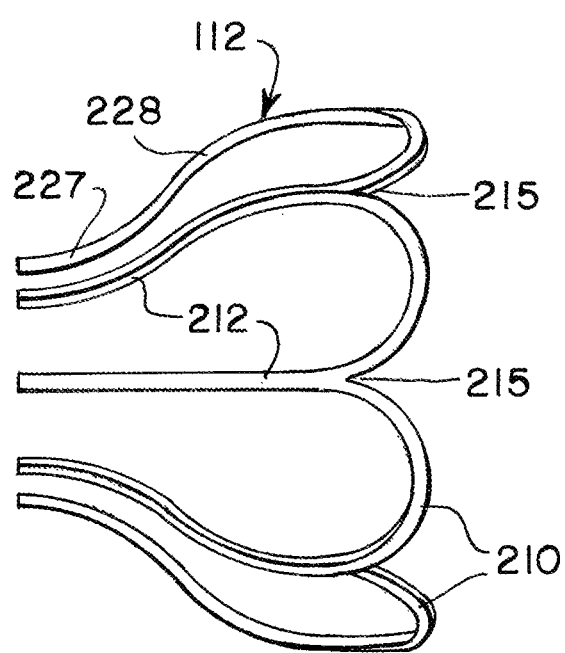
Figure 16A:
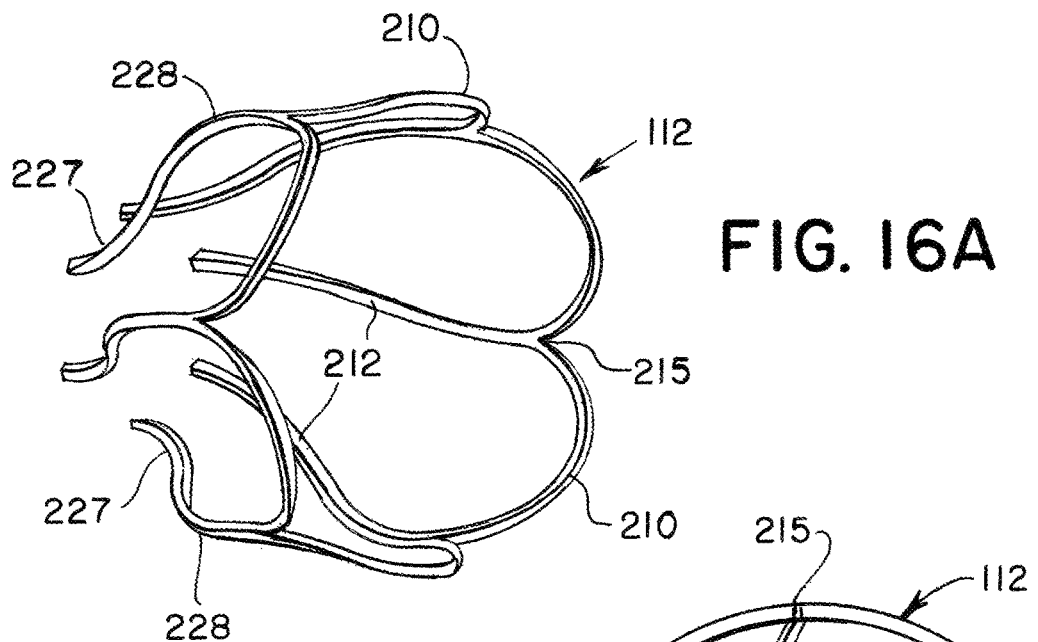
Figure 16B:
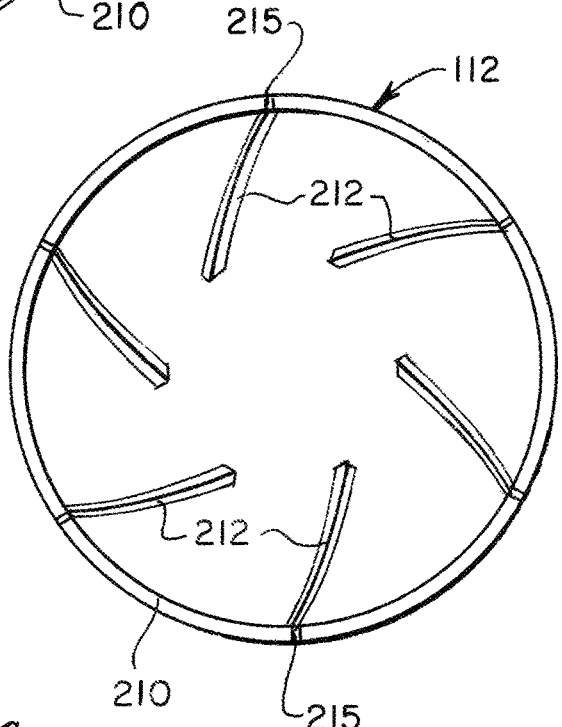
Figure 16C:
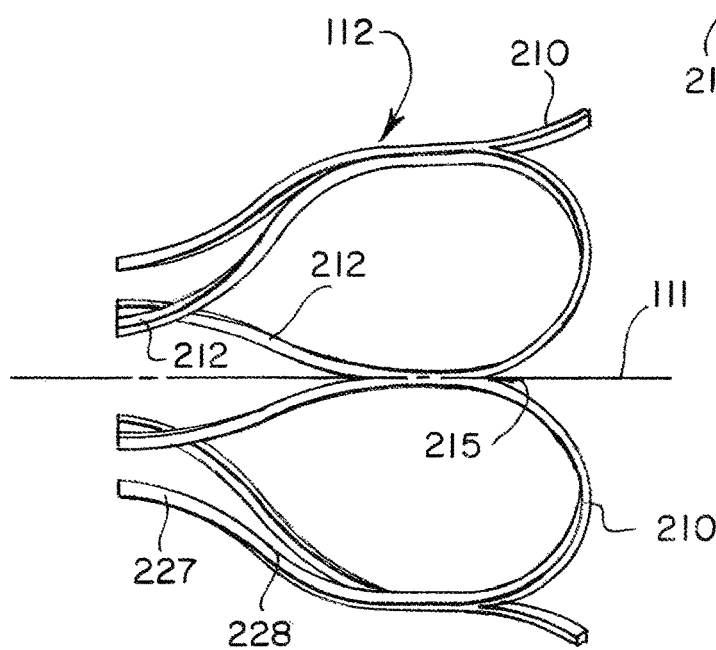
Figure 17C:
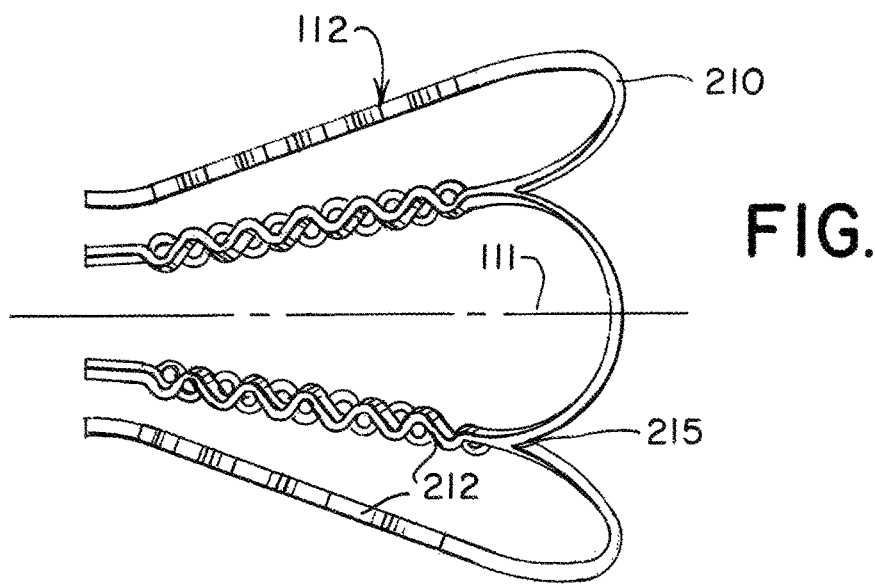
Figure 17D:
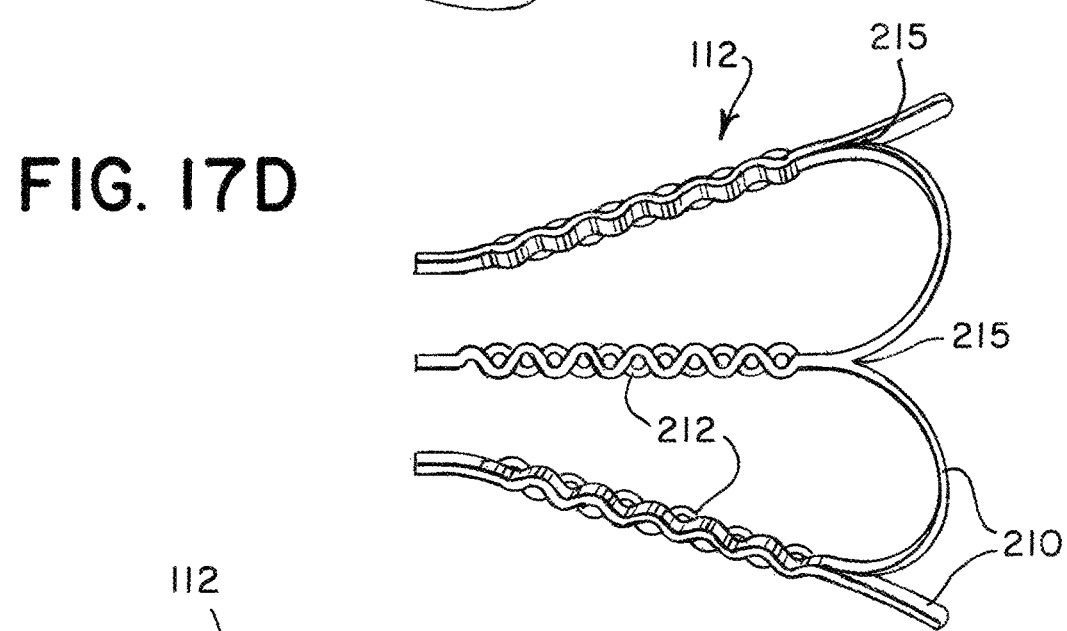
Figure 18A:
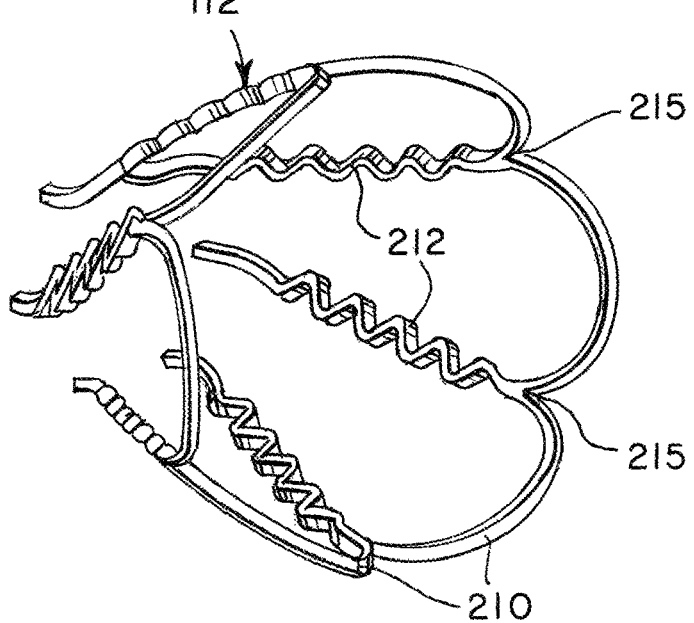
FIGS. 18A-18D are a series of views of another expansile tip framework according to aspects of the present invention.
Figure 18B:
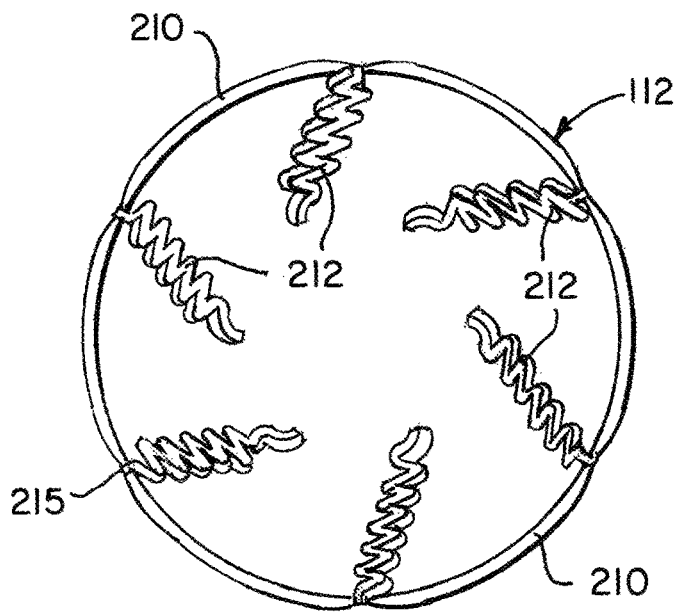
Figure 18C:
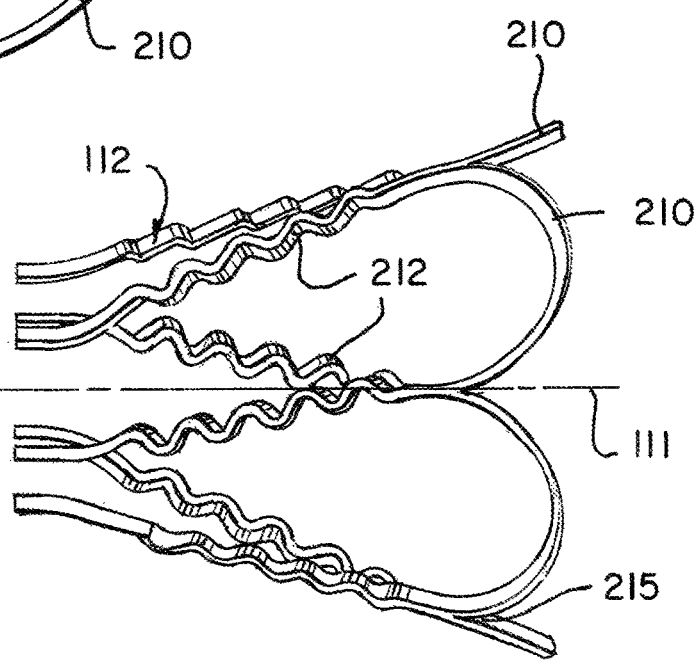
Figure 18D:
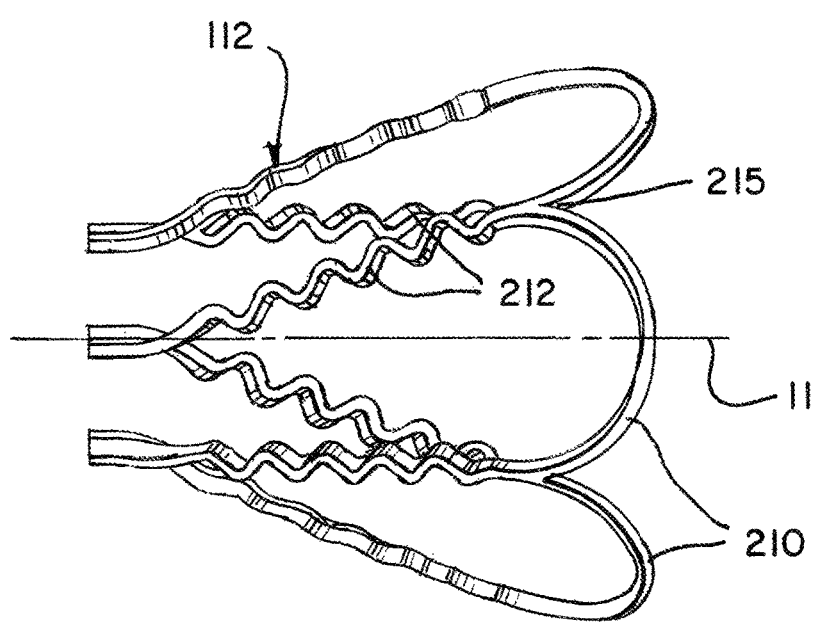

Another example of a tip framework 112 with eight crowns 210 and eight support arms 212 linked by proximal crown troughs 215 is shown in FIGS. 15A-C. The support arms extend longitudinally and can have at least two undulations or curves along their length. A proximal first curve 227 can be a concave curve facing an adjacent wall of a blood vessel and a second distal curve 228 can be a convex curve facing an adjacent wall of a blood vessel. The curves in the support arms 212 aid the arms in shortening and lengthening at opposite sides in a collapsed delivery configuration when being advanced through tortuous vessels to a target site. The curves also help when certain arms are not aligned with the bending plane of the clot retrieval catheter 110 as imposed by the blood vessel's shape by allowing the arms to flex and torque about the bending plane. Further, the curves, combined with an acute taper angle (<45 degrees) from the support tube 124 to maximum expanded diameter can also help to prevent the framework 112 from over expanding if the catheter 110 is pushed forward while the tip is expanded.

Referring to FIGS. 16A-D there is shown an expansile tip framework 112 with six crowns 210 and six support arms 212 disposed about a longitudinal axis 111 of the aspirating clot retrieval catheter 110. The support arms can have a helical arrangement with respect to the axis, allowing the support arms to torque as the arms shorten and lengthen during advancement (in a collapsed configuration) through bends and corkscrews in the vasculature. Similar to the previous example, the support arms can also have at least two curves along their length. A first proximal curve 227 can have a concave face facing an adjacent wall of a blood vessel and a second distal curve 228 can have a convex face facing and adjacent wall of the vessel. Having concave and convex curves help the support arms shorten and lengthen when navigating vessel paths. The curves also help prevent the tip framework from expanding too much if the device is pushed forward while the tip is in the expanded state.

FIGS. 17A-D shows another expansile tip framework 112 which also has six crowns 210 and six support arms 212 coming together at proximal crown troughs 215. The support arms can extend along a substantially conical surface in a smooth periodic oscillation of curves aligned with the longitudinal axis 111 of the clot retrieval catheter 110. The undulating curves of the support arms allow them to bend about their own axis, giving the tip framework additional flexibility when being delivered to a target site in the collapsed configuration. The circumferential undulations of the support arms also provide more support area to prevent collapse of the cover 118. The undulations may have a constant pitch and amplitude as shown or the pitch and amplitude can be varied to adjust the stiffness from the proximal to distal end of the support arms. Similar to other examples, trackability and flexibility can also be improved by making the support arms thicker or thinner in regions of the struts.

Views of a tip framework 112 with six crowns 210 and six support arms 212 with adjacent crowns coming together at proximal crown troughs 215 are illustrated in FIGS. 18A-D. The support arms can extend proximally from the proximal crown troughs and taper to form a substantially conical shape. The support arms can have periodic, sinusoid-like undulations along their length which allows the arms to flex about their own axis, giving the tip framework additional flexibility for navigating tortuous vessels or for when the tip must be re-folded into the collapsed state when being withdrawn back in to the outer catheter. The undulations also provide additional structural support surface area for the cover 118. Further flexibility is gained by twisting the support arms in helical fashion about the longitudinal axis 111 of the clot retrieval catheter 110. A helical configuration facilitates and encourages tip rotation and bending through tortuous vessel anatomies.

FIGS. 19A-E shows several views of a version of the expansile tip framework 112 with six crowns 210 and two support arms 212 joined at proximal crown troughs 215. The two support arms can be spaced 180 degrees apart and can extend along a substantially conical surface with smooth periodic oscillations in a direction aligned with a central longitudinal axis 111. The oscillations allow the support arms to bend about their own axis and give the tip framework the flexibility to track easily through the outer catheter when in the collapsed delivery configuration.

The proximal ends of the support arms 212 can be formed integrally with the support tube 124. The support tube can have two or more axial spines 120 along the length of which a plurality of circular ribs 122 are disposed. If two spines are used, they would define a common bending plane of the clot retrieval catheter 110 lying on the longitudinal axis 111 and passing through the two spines. The spines can also be aligned with the support arms such that the expansile tip can easily bend along the same plane. The ribs and spines can have a uniform or variable thickness, allowing the tailoring of the stiffness profile along the length of the support tube.

Figure 19A:
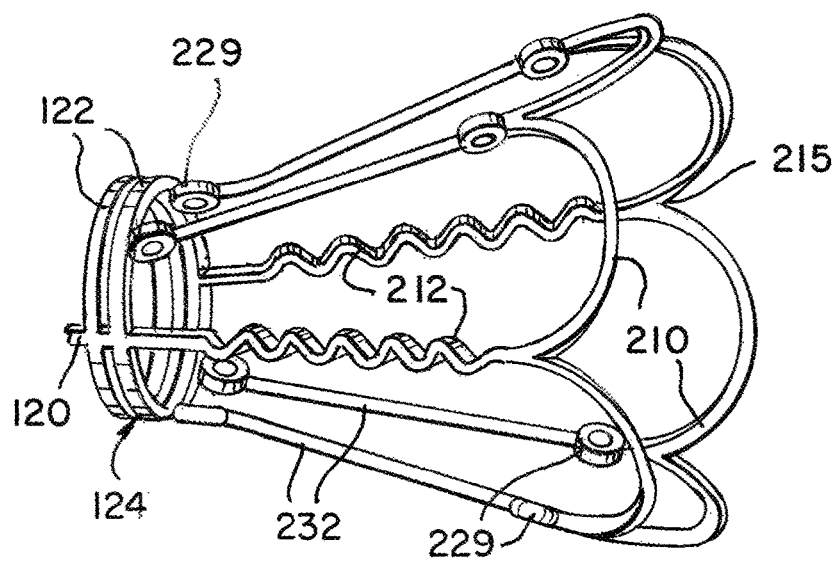
FIGS. 19A-19D are a series of views of another expansile tip framework according to aspects of the present invention.
Figure 19B:
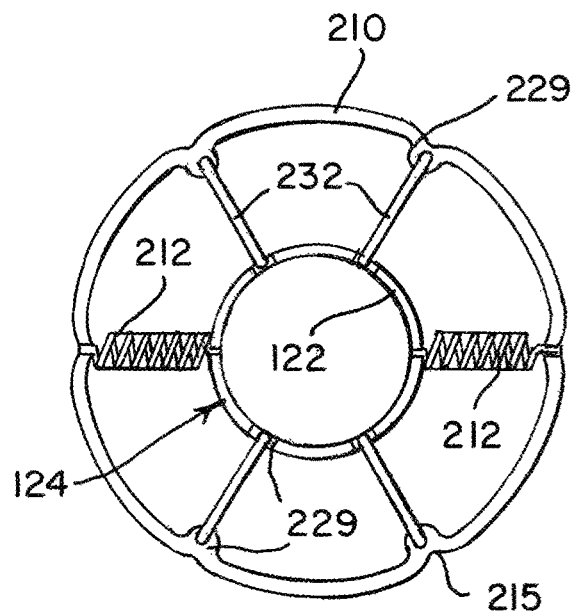
Figure 19C:
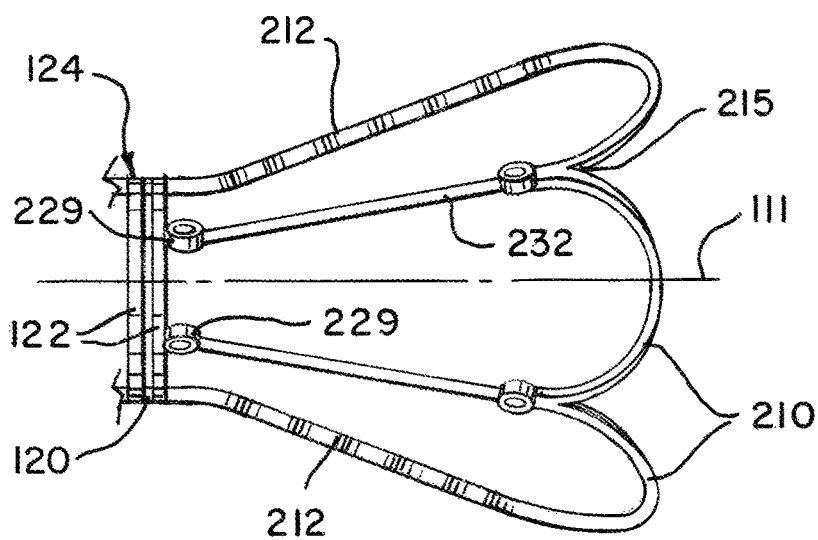
Figure 19D:
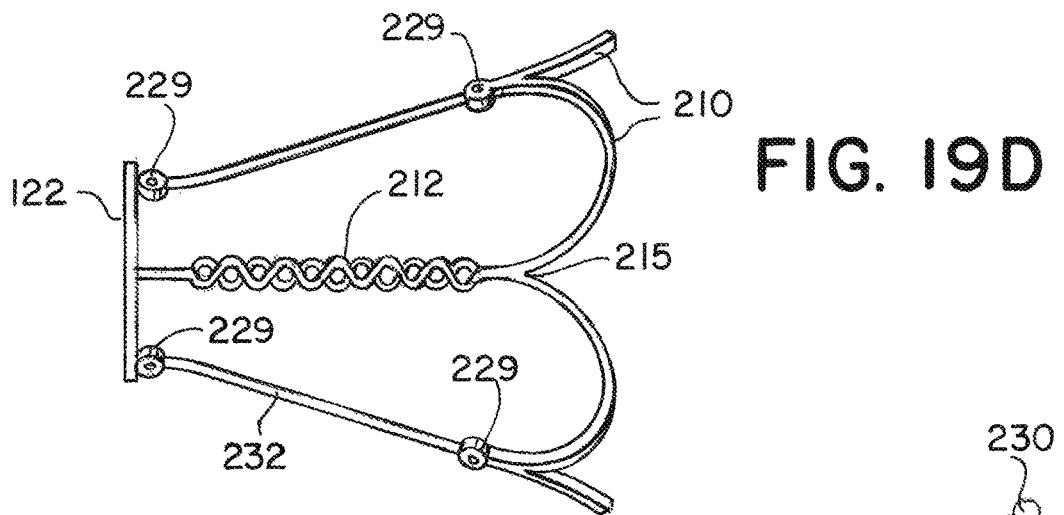
Figure 19E:
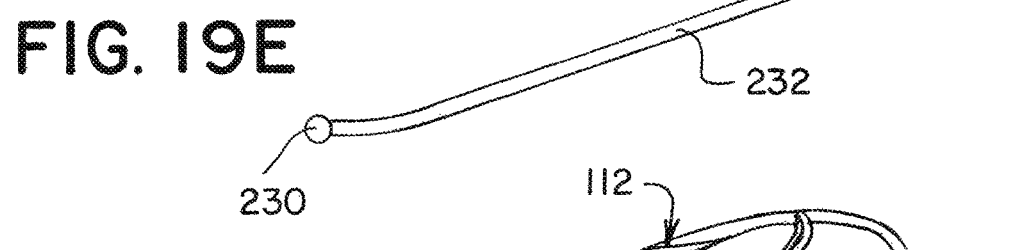
FIG. 19E is a view of a string like member of the tip of FIG. 19A according to aspects of the present invention.
Figure 20A:
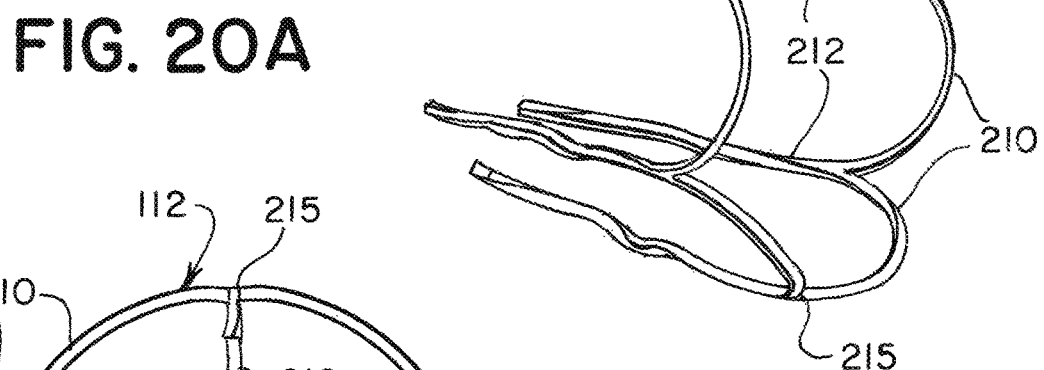
Figure 20B:
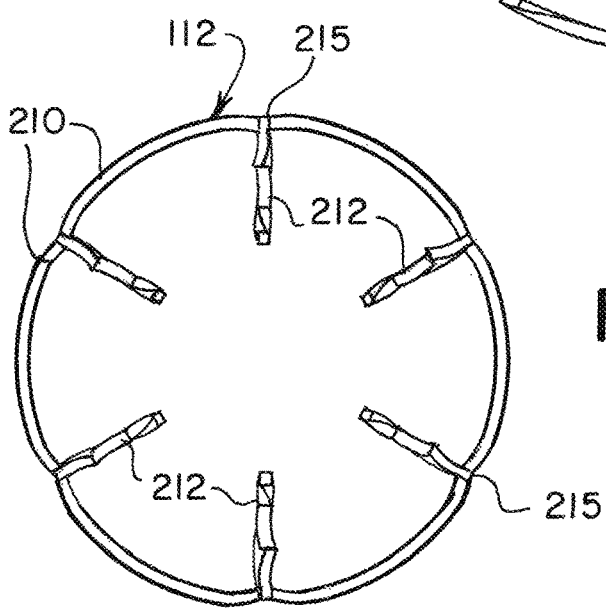
Figure 22A:
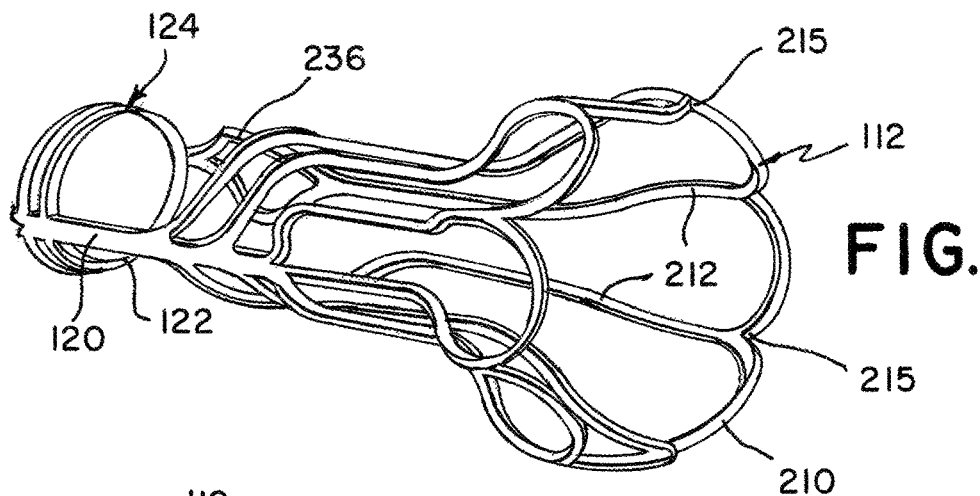
FIGS. 22A-22D are a series of views of another expansile tip framework according to aspects of the present invention.
Figure 22B:
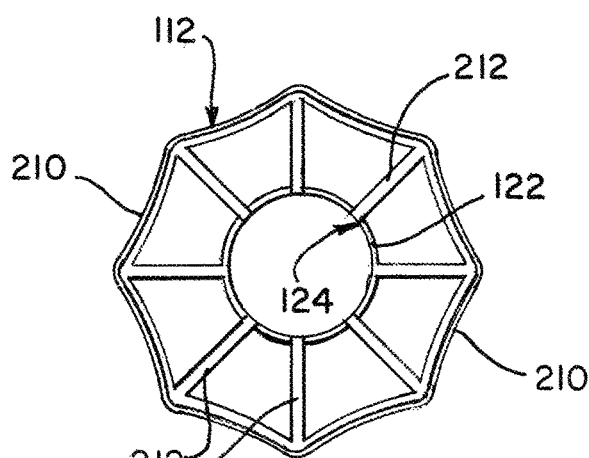
Figure 22C:
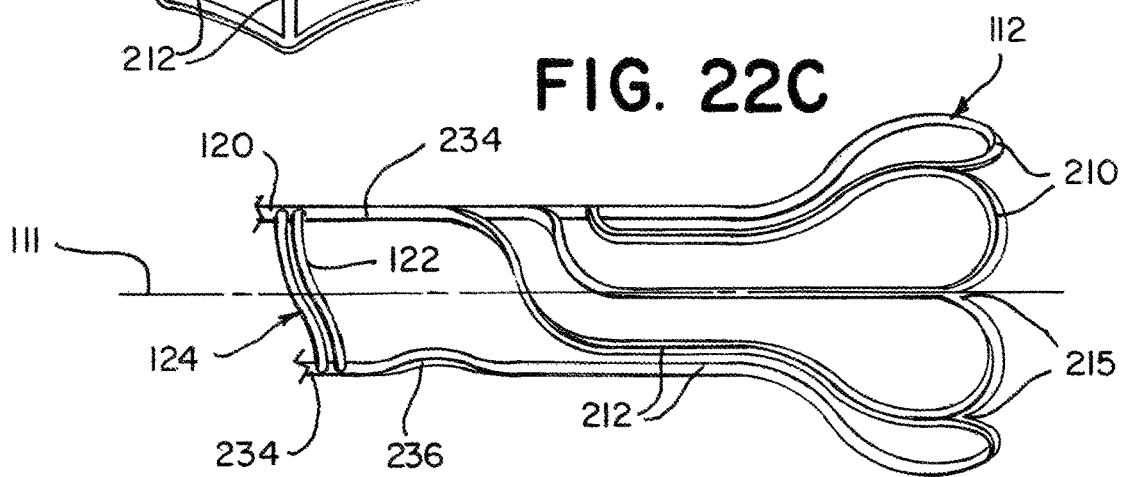
Figure 22D:
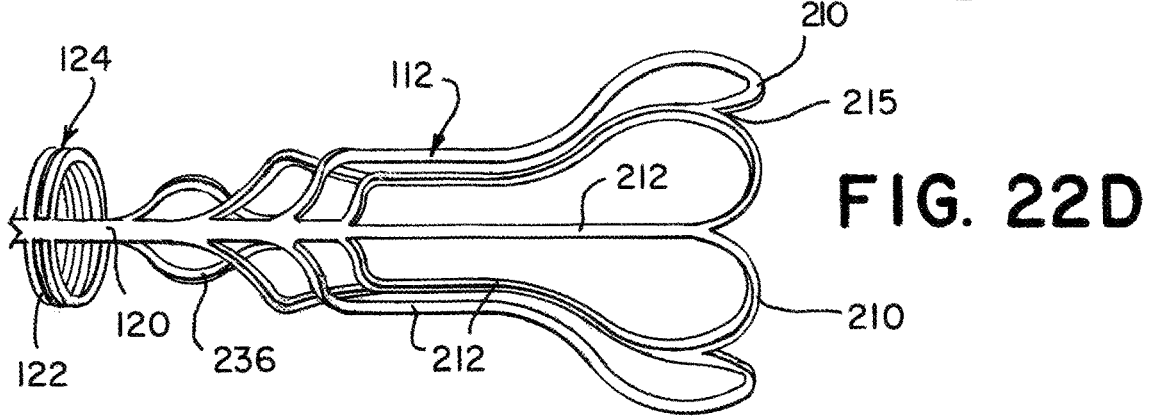

In this example, further support for the cover 118 at the expansile tip 200 can be provided by string-like member strut 232 non-rigidly connecting the expansile tip framework 112 and support tube 124. In one example, four string-like members can be disposed around the longitudinal axis 111 spaced evenly between the support arms 212 such that they are approximately 60 degrees apart. Instead of a direct connection, the string-like members can be threaded through eyelets 229 located at the proximal crown troughs 215 and attached to the distalmost rib of the support tube, as seen in FIGS. 19A-D The string-like members can be secured in place with an enlarged bulb 230 at opposing ends of the string-like members 232, as shown in FIG. 19E. The bulb ends can be formed during manufacturing after the string-like member had been fed through the associated eyelets by any of a number of methods, such as forming a knot, applying heat, or with mechanical plastic deformation. The string-like members aid in supporting a cover and in providing a smooth transition during retraction of the expansile tip between a mouth of an outer catheter and the proximal troughs 215 of the crowns which are not directly connected to the support tube by the support arms 212. By having only two rigid support arms spaced 180 degrees apart, the tip can bend about the bending plane when being advanced to a target site through the outer catheter.

In another example of an expansile tip framework 112 shown in FIGS. 20A-D, there can be six crowns 210 and six support arms 212 that are laser-cut from a shape memory alloy in a sinusoidal pattern before the tip framework is expanded and shape set to be a substantially conical shape during manufacture. During the shape setting process, the support arms can be twisted about their axes between the proximal connection to the support tube and the distal connection to a proximal crown trough 215 such that the curves undulate in a radial direction rather than the circumferential direction they are cut in. The angle of twist can be 90 degrees, as shown in the figures, or can be some other angle. Additional offset twists can be added to each arm if desired. Radial undulations can allow the support arms to bend more easily when the aspirating clot retrieval catheter 110 is tracked through an outer catheter in tortuous areas of the vasculature. In other examples, the bending properties of the tip framework 112 can be tailored by only twisting a subset of the support arms 212, or by incorporating different twist angles and twist directions.

Multiple views of an expansile tip framework 112 with eight crowns 210 and eight support arms 212 adjoined together at proximal crown troughs 215 are shown in FIGS. 21A-D. The support arms can extend independently from the proximal crown troughs of the distal crowns to a single connecting strut 234 that is aligned with an axial spine 120 of a support tube 124. The support tube can have a single axial spine for added flexibility, while having circular, semicircular, or other shape ribs 122 to support the cover 118.

The connecting strut 234 can be configured such that the support arms 212 intersect at different points along the length of the connecting strut, giving additional flexibility for the support arms. The added flexibility can allow the support arms to expand radially outward as a clot is being retrieved, providing a larger mouth for aspiration and clot reception which would result in a higher success rate when extracting stiff clots. The support arm 212 expansion can further stretch the cover 118 while aspirating and withdrawing the clot retrieval catheter 112 and clot into the distal tip of the outer catheter 30.

FIGS. 22A-D shows several views of a version of an expansile tip framework 112 with eight crowns 210 and eight support arms 212. The support arms extend distally from proximal crown troughs 215 to intersect with one of two connecting struts 234 spaced 180 degrees apart across the diameter of the support tube 124. The support tube can have multiple axial spines 120 aligned with the connecting struts, or a single axial spine aligned with a first connecting strut, and the opposite second connecting strut connected to a distal peak of the most distal support rib 122. The connecting struts can split distal of their connection to the support tube and rejoin at a further distal distance to connect to at least one support arm 212. The split or splits create a closed expansion cell or cells 236 which can lengthen longitudinally to reduce the likelihood of the ribs 122 of the support tube 124 pulling the crowns 210 of the expanded tip framework proximally while aspirating during retraction of a clot.

The crown struts 210 which form the mouth of the tip framework 112 can have a curve that extends radially inward at the distal end. This can reduce the risk of the tip snagging on capillary vessel openings or from exerting forces into the vessel wall if the clot retrieval catheter 110 is advanced distally through a vessel with the tip in the expanded deployed configuration. The curves can thus help the tip glide along the vessel wall without the risk of vessel damage or perforation. To further enhance the catheter's ability to be advanced distally without causing tissue damage while the tip is expanded, the angle between an edge of the substantially conical or funnel-shaped tip framework 112 and the central longitudinal axis 111 of the catheter can be less than 45 degrees. An angle of less than 45 degrees can bias the tip to collapse slightly during advancement of the clot retrieval catheter. An angle greater than 45 degrees can otherwise bias the tip to expand in diameter during advancement in a blood vessel, increasing the risk of snagging on or abrading with the vessel wall. An angle of less than 45 degrees is therefore desirable, and more preferably between 5 and 30 degrees.

The radial inward curve of the crown struts 210 can mean that the tip framework 112 can have a first radial dimension at the proximal end, a second radial dimension at an intermediate location, and a third radial dimension at the distal end, where the second radial dimension is larger than the first and third radial dimensions. When expanded and unconstrained, the diameter of the tip framework can range from 1 mm to 10 mm, and preferably from 3 mm to 6 mm, at the intermediate location for a device intended to treat blockages in the ICA, Carotid Terminus, M1 and M2 locations. The third radial dimension can be larger than the first radial dimension but smaller than the second radial dimension to provide an atraumatic tip.

Figure 23:
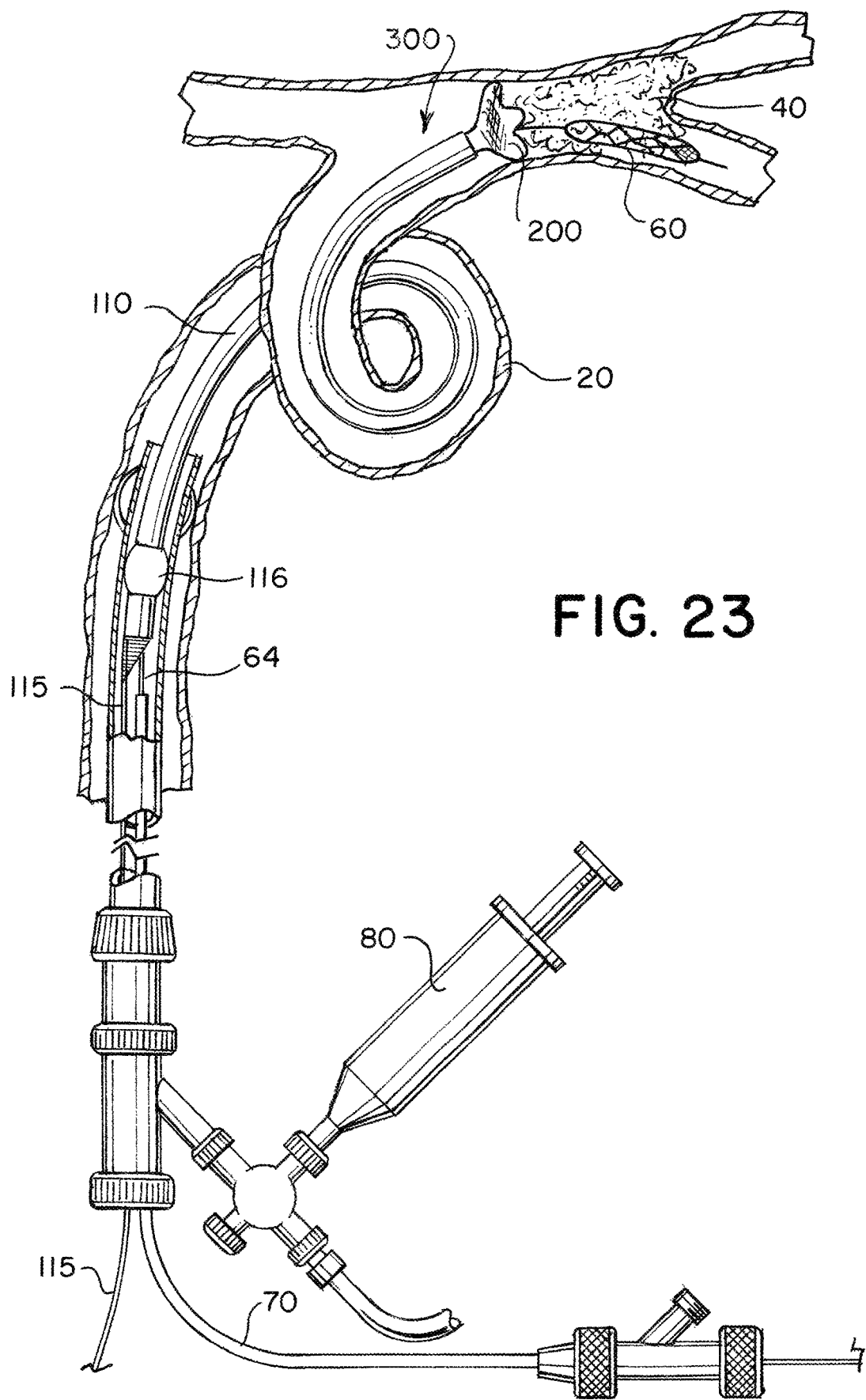
FIG. 23 is an illustration of an expansile tip aspirating clot retrieval system used in conjunction with a thrombectomy device, according to aspects of the present invention.

In some instances, dislodging or fully retrieving a clot using aspiration alone is not possible. Referring to FIG. 23, there is illustrated a system 300 with an aspiration clot retrieval catheter 110 and a mechanical thrombectomy device 60, or stentriever. The catheter 110 can be similar to that of FIG. 2 in that it provides an enlarged proximal segment 250 or seal 116 against the inner wall of the outer catheter 30 so that aspiration by a source 80, such as a syringe or pump, can be applied to the outer catheter and transferred through to the expansile tip 200 of the clot retrieval catheter 110. A thrombectomy device 60 is shown deployed within a clot 40, having been delivered through a microcatheter 70 and manipulated with a proximal device shaft 64. The shaft 64 can be fitted with a proximal torque device (not shown) to help a physician control and grip the shaft. The thrombectomy device 60 can be any of a number of commercially available products which can be supplied with or separate from the aspirating clot retrieval catheter.

Using a thrombectomy device in conjunction with an expanding mouth clot retrieval catheter has several benefits to increase the likelihood of first-pass success. The thrombectomy device can support the lumen of the vessel during aspiration such that it will be less likely to collapse under negative pressure, and the thrombectomy device will hold the clot together should the clot comprise an array of stiff and soft portions that may otherwise fragment. The thrombectomy device can also allow the user to pinch a clot that otherwise would not fully enter the lumen of the clot retrieval catheter between the catheter tip and thrombectomy device. A pinched clot will be less likely to dislodge from the clot retrieval catheter as the clot retrieval catheter, clot, and thrombectomy device are retracted as one through the vasculature and outer catheter. In this case, the interaction between the outer catheter and the expanded mouth will aid in compressing the clot so that it can be pulled through the outer catheter with the clot retrieval catheter and thrombectomy device. If the clot is also too large to enter the outer catheter, the outer catheter, clot retrieval catheter, thrombectomy device and clot can be retracted proximally through the vessel and into a larger proximal catheter such as a balloon guide. Should the clot still be too stiff to retrieve through the larger proximal catheter, all devices can be retracted together as one through the vasculature and outside of the body.

In one example, the thrombectomy device can be forwarded to the target site using a microcatheter 70 within the lumen of the clot retrieval catheter 110 and deployed distal of the expansile tip 200 by retracting the microcatheter, as illustrated in FIG. 24. Upon capture of a clot, the thrombectomy device can be withdrawn into the expansile tip 200, where the funnel shape may compress the structure of the thrombectomy device and enhance the grip exerted on the clot during retrieval. The expansile tip can also prevent snagging or shearing of the clot on the devices and catheters. In instances where access to the target site can be maintained through the aspirating clot retrieval catheter 110 and/or outer catheter 30 while the thrombectomy device is retrieved, aspiration can prevent the distal migration of any clot debris which is liberated. If additional retrieval attempts are needed to clear the vessel, the microcatheter 70 and thrombectomy device 60 can then be quickly delivered back to the target site.

The thrombectomy device 60, microcatheter 70, clot retrieval catheter 110, and clot 40 can be retrieved beyond the distal end 72 and fully into the lumen 32 of the outer catheter 30. The clot retrieval catheter 110 and expansile tip 200 may be designed to work with an outer catheter 30 such as a 7Fr, 8Fr, 9Fr or 10Fr long guide sheath or balloon guide sheath. Alternatively, the clot retrieval catheter 110 may be designed to work with an outer catheter 30 such as a 4Fr, 5Fr, or 6Fr intermediate catheter.

The aspiration source 80 can be a manual syringe or a small-displacement vacuum pump and aspiration directed to the distal tip of the clot retrieval catheter 110. Effective aspiration can be accomplished by the sealing action of the expansile tip 200 with the vessel walls or the interior walls of the outer catheter, and/or through the use of an enlarged proximal segment 250 or flow restrictor/seal 116 of the retrieval catheter. Restricting flow between the catheters can unite the outer catheter lumen 32 with the lumen 113 of the clot retrieval catheter 110 to ensure the maximum flow rate and pressure drop are transmitted to the proximal port 117. In addition, blood can be prevented from entering the tip of the outer catheter 30, which would hinder the efficiency of the aspiration. An enlarged segment 250 or seal 116 may not need to be completely hermetic, but it needs to restrict flow appreciably such that sufficient aspiration is available at the target location.

In one example shown in FIG. 25A, a seal 116 can be located on the outer surface of the clot retrieval catheter 110 and activated to expand radially outward to the inner wall of the outer catheter 30. In an alternate configuration shown in FIG. 25B, the seal 116 can be located on the inner wall of the outer catheter 30 and activated to expand radially inward to the outer surface of the clot retrieval catheter 110.

FIGS. 25A and 25B also illustrate a further case where another flow restriction or seal 50 can be configured between the inner wall of the vessel 20 and the outer wall of either the outer catheter 30 or the clot retrieval catheter 110. This can be useful in a case where the funnel mouth cover or membrane 118 of the expansile tip 200 is porous, allowing seal 50 can be opened or closed in order to inject contrast through the funnel of the expansile tip 200. The contrast can be allowed to flow to the clot and back through the porous funnel and proximal reaches of the vessel with aspiration so as to not push the clot distally. The seal 50 can then be closed to block flow so that the clot can be aspirated efficiently.

In other embodiments a seal is not required. The catheters can be sized so the lumen between the inner diameter of the outer catheter and the outer diameter of the aspirating clot retrieval catheter is small enough for aspiration losses to be negligible. Similarly, a portion of the clot retrieval catheter can flare to a larger diameter to restrict or block flow, or a portion of the body of the clot retrieval catheter can be coated with a hydrogel that swells with hydration in order to achieve a seal with the inner surface of the outer catheter. Alternatively, the lumen between the outer diameter of the clot retrieval catheter and the inner diameter of the outer catheter can be set such that aspiration is applied at two locations, both the distal end of the clot retrieval catheter and the distal end of the outer catheter.

Figure 26:
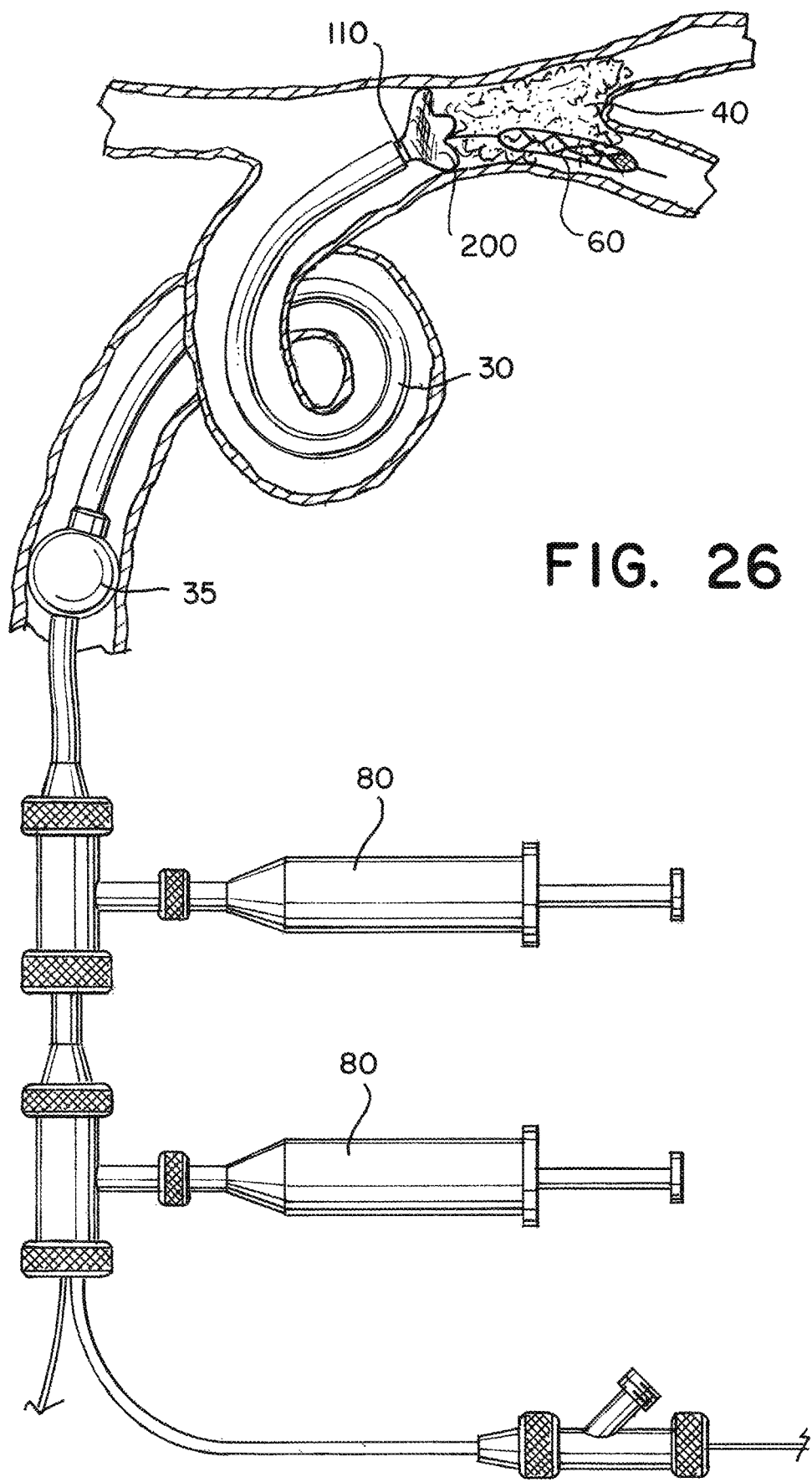
FIG. 26 is an illustration of an expansile tip aspirating clot retrieval system used in conjunction with a mechanical thrombectomy device and a balloon guide catheter, according to aspects of the present invention.

As illustrated in FIG. 26, the systems can also be used with a balloon guide catheter 35 serving as an outer sheath for the outer catheter 30 and the aspirating clot retrieval catheter 110. As with other examples, a thrombectomy device 60 can be employed to dislodge and grip the clot 40. One or more aspiration sources 80 can be connected at the proximal end of the system to draw a vacuum through any combination of the balloon guide catheter, outer catheter, and/or aspirating clot retrieval catheter. When inflated, the balloon can arrest blood flow and secure the balloon guide catheter 35 in place for treatment.

FIG. 27 and FIG. 28 are flow diagrams each comprising method steps for performing a thrombectomy procedure with such a system. The method steps can be implemented by any of the example systems, devices, and/or apparatus described herein or by a means that would be known to one of ordinary skill in the art.

Referring to a method 2700 outlined in FIG. 27, step 2710 describes the task of providing and positioning an outer catheter and an inner clot retrieval catheter, the clot retrieval catheter comprising a self-expandable tip, a support tube comprising a hollow structure disposed around a longitudinal axis of the clot retrieval catheter, a cover disposed around the expandable tip and support tube, and a distal mouth. The outer catheter can be supplied with the clot retrieval catheter or can be a compatible product known in the art. The self-expandable tip can be sized when unconstrained to be the same or of a slightly larger diameter than a target blood vessel containing an occlusive clot or thrombus so that the tip can seal with the vessel and provide local flow restriction/arrest when deployed. In step 2720, a flow restriction or seal may be provided between the inner wall of the outer catheter and the outer wall of the clot retrieval catheter to link their respective lumens and direct more efficient aspiration to the clot. The step can involve the use of a flared or enlarged proximal segment or an activatable seal to restrict/arrest flow, or another approach commonly used in the art. In step 2730, at least a portion of the clot retrieval catheter can be provided with low-friction and/or lubricious properties, through a surface treatment, coating, or similar practice. A coating, for example, can be applied by spray, reflow, injection molding, or ion transportation/plasma. One of skill in the art can also appreciate that a coating step may be unnecessary if the tip and/or cover is made from a material that already exhibits low-friction properties.

In step 2740, the perimeter of the distal mouth of the clot retrieval catheter can be covered with a soft elastomeric lip with large edge radii or can be coated or encapsulated in a compliant material for atraumatic contact with vessel walls. In step 2750, access is gained to an arterial blood vessel of a patient using conventional, well-known means.

Referring the method 2800 outlined in FIG. 28, in step 2810, the inner clot retrieval catheter is situated in the lumen of the outer catheter and the catheters are advanced into and through the vasculature to the location of the occlusive clot. In step 2820, the inner clot retrieval catheter is deployed from the outer catheter adjacent to the clot to radially expand the expansile tip. Aspiration can then be applied through one or both of the outer catheter and clot retrieval catheter in step 2830, depending on how the user has deployed the flow restrictions and/or seals, to stimulate the clot into the mouth of the clot retrieval catheter. If aspiration alone is insufficient to dislodge and capture the thrombus or if additional grip on the clot is desired during initial aspiration and dislodgement, a microcatheter with a mechanical thrombectomy clot retrieval device can be advanced to the target in step 2840. The mechanical thrombectomy device can then be deployed to capture the clot using any method commonly known in the art. Aspiration can continue during the entirety of this step to prevent blood reflux and maintain a tight grip on the clot, or at intervals chosen by the user. In step 2850, the captured clot and clot retrieval catheter can be withdrawn from the patient or the clot retrieval catheter can be left in place to maintain access as the mechanical thrombectomy clot retrieval device is withdrawn with the clot from the patient. If the clot is observed in the aspiration source and/or thrombectomy device and flow is not blocked in the clot retrieval catheter, this step can also involve carefully injecting contrast under low pressure through the system using known techniques to determine if the vessel is patent. The user may further desire to collapse the expanded mouth of the clot retrieval catheter prior to injecting contrast by retracting the tip into the outer catheter, so that any remaining debris is not inadvertently pushed distally. If the vessel is patent, the clot retrieval catheter can be removed. If a blockage remains, additional passes of aspiration, thrombectomy or a combination of these may be repeated until the vessel is patent.

The invention is not necessarily limited to the examples described, which can be varied in construction and detail. The terms "distal" and "proximal" are used throughout the preceding description and are meant to refer to a positions and directions relative to a treating physician or user. As such, "distal" or "distally" refer to a position distant to or a direction away from the physician. Similarly, "proximal" or "proximally" refer to a position near to or a direction towards the physician. Furthermore, the singular forms "a", "an", and "the" include plural referents unless the context clearly dictates otherwise.

As used herein, the terms "about" or "approximately" referring to any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that some of the method steps may be omitted.

The mention of one or more components in a device or system does not preclude the presence of additional components or intervening components between those components expressly identified. For clarity and conciseness, not all possible combinations have been listed, and such modifications are often apparent to those of skill in the art and are intended to be within the scope of the claims which follow.

The invention claimed is:

1. A system for retrieving an obstruction in a blood vessel, the system comprising:
   an outer catheter; and
   an inner clot retrieval catheter disposed within the outer catheter, the inner clot retrieval catheter comprising:
      an expansile tip comprising a porous framework and an open distal mouth disposed at the distal end of the expansile tip, the expansile tip having a folded delivery state and an expanded deployed state;
      a support tube proximal to the expansile tip comprising:
         two longitudinally extending spines located on opposing sides of the support tube;
         a plurality of loop ribs connected along the length of each of the two spines and external to each of the two spines, the loop ribs being axisymmetric with a longitudinal axis of the inner clot retrieval catheter and defining a lumen of the inner clot retrieval catheter extending therethrough; and
      a cover radially disposed around at least a portion of the support tube and at least a portion of the expansile tip;

wherein the expansile tip has a radial dimension in the folded delivery state less than a maximum radial dimension of the expansile tip in the expanded deployed state;

wherein in the expanded deployed state, the expansile tip is self-expanded from the folded delivery state to project radially outwardly of the support tube with at least a portion of the expansile tip having the maximum radial dimension of the expansile tip; and wherein the maximum radial dimension of the expansile tip is greater than an inner diameter of the outer catheter.

2. The system of claim 1, wherein, in the folded delivery state, at least a portion of the expansile tip between a proximal end and a distal end and the outer catheter have a common radial dimension.

3. The system of claim 1, wherein in the expanded deployed state the expansile tip is tapered such that a proximal end of the expansile tip has a first radial dimension and a portion of the expansile tip approximate the distal end has a second radial dimension larger than the first radial dimension;

wherein when the expansile tip is unconstrained, the second radial dimension is sized to be larger than the inner diameter of the blood vessel.

4. The system of claim 1, wherein the porous framework of the expansile tip further comprises:

a plurality of crowns and a plurality of support arms terminating in proximal crown troughs;

wherein in the folded delivery state the framework folds about the proximal crown troughs; and wherein the cover is radially disposed around at least a part of the framework.

5. The system of claim 4, wherein the framework further comprises one or more narrowed segments.

6. The system of claim 4, wherein each of the plurality of support arms of the porous framework comprise radial undulations.

7. The system of claim 4, wherein at least one of the two spines of the support tube is respectively aligned with a support arm of the plurality of support arms.

8. The system of claim 1, further comprising a dip zone defining a length of the framework encased by a low-friction elastomeric lip.

9. The system of claim 1, wherein the framework is at least partially encapsulated by the cover.

10. The system of claim 1, wherein the cover is adhered to the framework.

11. The system of claim 1, wherein the inner clot retrieval catheter further comprises a tubular liner disposed within and lining a lumen of the support tube.

12. The system of claim 1, wherein the cover further comprises one or more polymer jackets.

13. The system of claim 12, wherein at least one of the one or more polymer jackets is impregnated with particles having material properties to decrease a surface's coefficient of friction.

14. The system of claim 1, wherein at least a portion of the support tube is coated with a lubricious low-friction coating.

15. The system of claim 1, wherein at least a portion of the cover is permeable.

16. A method of retrieving an occlusive thrombus from a blood vessel of a patient comprising the steps of:

providing an outer catheter and an inner clot retrieval catheter, the inner clot retrieval catheter comprising:

a self-expandable tip, a support tube comprising:

a hollow structure disposed around a longitudinal axis of the inner clot retrieval catheter;

two longitudinally extending spines located on opposing sides of the support tube;

a plurality of loop ribs connected along the length of each of the two spines and external to each of the two spines, the loop ribs being axisymmetric with the longitudinal axis;

a cover disposed around the self-expandable tip and the support tube, and a distal mouth;

restricting flow in a lumen between at least a portion of an inner wall of the outer catheter and at least a portion of an outer wall of the inner clot retrieval catheter;

accessing an arterial blood vessel of a patient using conventional means;

advancing the outer catheter and inner clot retrieval catheter to a target site;

deploying the inner clot retrieval catheter adjacent to the occlusive thrombus to radially expand the self-expandable tip;

aspirating through one or both of the outer catheter and inner clot retrieval catheter to stimulate the occlusive thrombus into the distal mouth of the inner clot retrieval catheter and capture the occlusive thrombus; and withdrawing the inner clot retrieval catheter with the captured occlusive thrombus from the patient.

17. The method of claim 16, further comprising the step of covering a perimeter of the distal mouth with an elastomeric lip.

18. The method of claim 16, further comprising: covering at least part of the inner clot retrieval catheter with a low-friction coating.

19. The method of claim 16, further comprising the step of capturing the occlusive thrombus with a mechanical thrombectomy device and withdrawing the mechanical thrombectomy device into the distal mouth of the inner clot retrieval catheter.

* * * * *